United States Patent
Agarwal et al.

(10) Patent No.: US 10,615,332 B2
(45) Date of Patent: Apr. 7, 2020

(54) MONITORING USING PIEZO-ELECTRIC CABLE SENSING

(71) Applicants: Anuj Agarwal, Lexington, KY (US); Michael E. Lhamon, Lexington, KY (US)

(72) Inventors: Anuj Agarwal, Lexington, KY (US); Michael E. Lhamon, Lexington, KY (US)

(73) Assignee: Signal Solutions, LLC, Lexington, KY (US)

( * ) Notice: Subject to any disclaimer, the term of this patent is extended or adjusted under 35 U.S.C. 154(b) by 344 days.

(21) Appl. No.: 15/592,765

(22) Filed: May 11, 2017

(65) Prior Publication Data

US 2018/0325384 A1    Nov. 15, 2018

(51) Int. Cl.
| | |
|---|---|
| A01K 29/00 | (2006.01) |
| H01L 41/45 | (2013.01) |
| H01L 41/087 | (2006.01) |
| H01L 41/193 | (2006.01) |
| A61B 5/113 | (2006.01) |
| A61B 5/00 | (2006.01) |
| A61B 5/08 | (2006.01) |

(52) U.S. Cl.
CPC ........... *H01L 41/45* (2013.01); *A01K 29/005* (2013.01); *A61B 5/113* (2013.01); *A61B 5/4812* (2013.01); *A61B 5/4818* (2013.01); *H01L 41/087* (2013.01); *H01L 41/193* (2013.01); *A61B 5/0816* (2013.01); *A61B 5/6888* (2013.01); *A61B 5/6892* (2013.01); *A61B 2503/40* (2013.01)

(58) Field of Classification Search
CPC ........ A01K 29/00; A01K 29/005; A01K 1/03; A01K 1/031
See application file for complete search history.

(56) References Cited

U.S. PATENT DOCUMENTS

| | | | | |
|---|---|---|---|---|
| 2006/0137621 | A1* | 6/2006 | Foresman | A01K 1/033 119/482 |
| 2007/0120667 | A1* | 5/2007 | Mainini | G08B 13/122 340/565 |
| 2007/0205893 | A1* | 9/2007 | Mainini | G08B 13/126 340/565 |
| 2008/0061970 | A1* | 3/2008 | Imai | G08B 13/08 340/545.1 |
| 2016/0113246 | A1* | 4/2016 | Donohue | A01K 29/005 702/139 |
| 2016/0217664 | A1* | 7/2016 | Bradford | E04F 15/02 |

OTHER PUBLICATIONS

Donohue et al., "Assessment of a non-invasive high-throughput classifier for behaviours associated with sleep and wake in mice," Apr. 11, 2008, BioMedical Engineering OnLine, pp. 1-4.

* cited by examiner

*Primary Examiner* — Kristen C Hayes
(74) *Attorney, Agent, or Firm* — Stockwell & Smedley, PSC

(57) ABSTRACT

Sensing an environment by confining a monitored live subject in an enclosure, detecting an effect on a coaxial piezoelectric cable resulting from the monitored live subject, wherein the coaxial piezoelectric cable is located at least proximate to the enclosure, and deriving information about a state of the monitored live subject based on the detected effect.

19 Claims, 24 Drawing Sheets

X-Axis (e.g. Score, range -6 to +6)

MONITORING USING PIEZO-ELECTRIC CABLE SENSING

SPONSOR STATEMENT

This invention was made with an award from the Kentucky Cabinet for Economic Development, Office of Commercialization and Innovation, under Grant Agreement KSTC-184-512-13-158 with the Kentucky Science and Technology Corporation. This invention was made with government support under 2R44NS083218 awarded by the National Institutes of Health. The government has certain rights in the invention.

FIELD OF THE INVENTION

The present invention relates generally to noninvasive sensing of certain physiological states and parameters and, more particularly doing so using a piezoelectric polymer manufactured into a coaxial cable.

BACKGROUND

The human body is a complex organism comprising several synchronized parts (e.g. organs) that adapt to the needs of the body in response to external stimuli. For example, the heart rate and breathing rate increase involuntarily in response to increased physical activity. An increase or decrease in ambient temperature makes us sweat or shiver. Understanding the mechanisms governing these intricate physiological phenomena aids in maintaining a healthy body and in prevention and cure of diseases.

Advancements in technology for measuring biosignals have increased our understanding of the physiological mechanisms. Medical research aimed at enhancing human health (e.g. drug development) widely uses animals as models for human disease. Physiological parameters derived from biosignals in animals often requires invasive techniques. For example, in rodents (rats, mice, etc.), bioelectric signals from the brain (electroencephalogram or EEG) and muscle activity (electromyogram or EMG) are obtained via electrodes embedded surgically in their skull. The surgery and post-surgery care limits their application to small scale studies. The information revealed by these biosignals can also be obtained by using alternate non-invasive methods (i.e. video recording), but have high implementation costs and generate unmanageably large amounts of data.

SUMMARY

Aspects of the present invention relate to a system for sensing an environment that includes an enclosure configured to confine a monitored live subject; a coaxial piezoelectric cable positioned at least proximate to the enclosure; a receiver circuit, in electrical communication with the coaxial piezoelectric cable, to receive a signal indicative of an effect on the coaxial piezoelectric cable resulting from the monitored live subject when the monitored live subject is within the enclosure; and a computer-readable memory, in electrical communication with the receiver circuit, to store data related to the signal received by the receiver circuit.

Aspects of the present invention relate to sensing an environment by confining a monitored live subject in an enclosure, detecting an effect on a coaxial piezoelectric cable resulting from the monitored live subject, wherein the coaxial piezoelectric cable is located at least proximate to the enclosure, and deriving information about a state of the monitored live subject based on the detected effect.

BRIEF DESCRIPTION OF THE DRAWINGS

Various aspects of the present invention are illustrated by way of example, and not by way of limitation, in the accompanying drawings.

DETAILED DESCRIPTION OF THE PREFERRED EMBODIMENTS

Figure 1A:
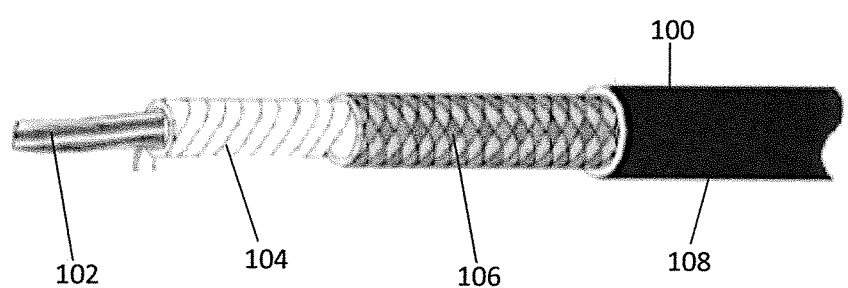
FIG. 1A depicts a diagram of a coaxial piezoelectric cable in accordance with the principles of the present invention.

The present invention relates to, but is not limited to, non-invasive sensing of physiological states and parameters using a piezoelectric sensor manufactured in a cable format, present in the vicinity of, or in contact with, a live subject such as a mammal.

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

In the description below, reference is made to a rodent by way of example only and one of ordinary skill will recognize that other functionally equivalent animals, such as any animal usable as a human model for disease, wherein the animal's fine movements (e.g. breathing and heartbeat) are detectable by piezoelectric sensor, may be used without departing from the scope of the present invention.

In the description below, "rodent" refers to any living being having position and/or movement, including motor movement, breathing, and/or heartrate, detectable by piezoelectricity. Pressure, vibration, and/or compression waves may be detectable by piezoelectricity.

In the description below, references to breathing and/or breath rate also refer to respiratory effort. Respiratory effort can be used to indicate activity/inactivity or other classifications.

In the description below, horizontal or vertical position is referenced relative to the plane of the floor of the cage.

In the description below, "experiment data" refers to one or more data sensed from a monitored subject within a cage a coaxial piezoelectric cable.

In the description that follows, the term "cage" is used to encompass a variety of different enclosures. A cage can include a typical cage that houses one or more rodents with solid perimeter walls located around a floor. Such a cage may have various sizes and shaped and may or may not include a lid. However, as used herein, a cage is intended to encompass any space occupied by a subject, such as a rodent, that is being observed.

A large number of laboratory animals are currently used in the US for research related purposes. A tremendous amount of money is spent in monitoring the health of these animals each year. The National Instituted of Health (NIH), in 2015, spent $10.19 million to feed and care for 573 chimpanzees. The coaxial piezoelectric cable system of the present invention is ideal for use in such animal facilities to aid in general health monitoring of these animals. As described herein, the cables can easily be incorporated into the tracks of a cage rack system meant for small animals or in enclosures of big animals and can be used to indicate the general well-being of the animal. Thus, the coaxial piezoelectric cable system disclosed can save personnel time and reduce maintenance and treatment costs.

Many animal studies are used to model human health and/or disease. The functioning of the human body is governed by complex physiological processes which may be modulated by environmental factors. Environmental stimuli such as light, temperature, food, physical activity, and social contact can play a role in governing human behaviors. For example, the absence or presence of light may make humans sleepy or awake; an increase or decrease in ambient temperature can make humans sweat or shiver; the availability or non-availability of food can decrease or increase the need for physical activity, etc.

Advancements in technology for measuring biosignals have increased understanding of the physiological mechanisms of behavior. Medical research aimed at enhancing human health commonly uses animals, such as rodents, as models for human disease. Measuring biosignals in animals often requires invasive techniques. For example, in rodents (rats, mice), bioelectric signals from the brain (electroencephalogram or EEG) and muscle activity (electromyogram or EMG) are obtained via electrodes embedded surgically in their skull. The surgery and post-surgery care limits their application to small scale studies. The information revealed by these biosignals can also be obtained by using alternate non-invasive ways (e.g. video recording), but the current methods have high implementation costs and generate a huge amount of data which gets difficult to manage.

One of the more necessary and least understood physiological functions (or behavior) is sleep. The phenomenon of sleep is a highly complex and well preserved function across mammals and is also seen in other species like reptiles, birds, fish, and some invertebrates. The exact reason and mechanisms of sleep are still unknown but it's widely accepted that it plays an important role in recovery from illness or injury, as well as memory and cognitive performance. The sleep circuitry and the electrophysiological rhythms in the brain of rodents, such as rats and mice, are similar to humans. Thus, bioelectric signals such as EEG and EMG can be used to quantify a sleep state of a rodent.

Many experiments involving mammal behavior have been performed using invasive or restrictive means. Invasive means include (EMG) and (EEG) because sensors must be implanted or ingested in the animal's body. Restrictive means may include any means requiring a wearable or tether, such as a collar, cuff, wire, or a blanket having a sensor, such as an accelerometer. However, restrictive means may alter rodent behavior due to restricted movement, restricted mobility, tethering, and/or added weight. Each of these invasive and restrictive means may alter rodent behavior due to stimuli resulting from surgery or restrictions on movement. Furthermore, these methods may produce large volumes of data, thereby requiring undue time and resources for processing the measured data.

Video is available as a non-invasive means of assessing rodent behavior, thereby allowing stimuli altering the rodent's behavior to remain limited to the stimuli intentionally introduced by the experimenter. However, conventional video constantly captures reflected light. Thus, some form of light must constantly illuminate the cage, which would require extra equipment and setup time. Also, special segmentation software is required to identify visible light pixels associated with the rodent and to track and interpret rodent movement. Furthermore, abnormalities in reflection of visible light may result in harmful outliers in the data collected. For example, special lighting may be required to minimize shadows. These shadows or reflections of light off the cage may interfere with the segmentation software to identify visible light pixels associated with the rodent. Finally, streaming video requires high data volume and therefore more processing resources.

Thus, embodiments of the present invention provide for the use of a coaxial piezoelectric cable for a sensor that can be fit to a variety of cages and platforms. In some embodiments, the coaxial piezoelectric cable can comprise polyvinylidene fluoride. Furthermore, the coaxial piezoelectric cable can be used to track sleep, activity, and other physiological functions in mammals.

A coaxial piezoelectric cable can use the piezoelectric effect to measure physical change by generation of a proportional electrical charge. Typically, changes in physical pressure result in generation of the electrical charge. Thus, piezoelectric sensors may measure and/or quantify changes in physical pressure. As mentioned above, an example material for a piezoelectric sensor can include a polyvinylidene fluoride based sensor within a coaxial cable.

In stark contrast to a coaxial piezoelectric cable, a conventional piezoelectric pressure sensor typically includes a thin membrane and a massive base to ensure that the applied pressure loads the element in one direction. The coaxial piezoelectric cable achieves the same effect by wrapping a thin piezoelectric film around the inner conductor of a coaxial cable. The piezoelectric film acts as a dielectric between the center core and the outer braid of the cable. The piezoelectric polymer, manufactured into a coaxial cable format, is commercially available (Measurement Specialties, VA).

FIG. 1A depicts a diagram of a coaxial piezoelectric cable in accordance with the principles of the present invention. Referring to FIG. 1A, the coaxial piezoelectric cable 100 has a center core 102. The center core 102 may comprise one or more electrically conductive metals, such as copper. The center core 102 may be covered by a piezoelectric film tape 104. For example, the piezoelectric film tape 104 may be spiral wrapped around the center core 102. The piezoelectric film tape 104 may comprise polyvinylidene fluoride (PVDF). The piezoelectric film tape 104 may be surrounded by a conductive braid 106. For example, the conductive braid 106 may comprise copper, or any, other conductive metals or mixture of metals. The conductive braid 106 may be encased by an insulative jacket 108. For example, the insulative jacket 108 may comprise polyethylene, rubber, or any other electrical insulator.

Unlike rectangular sheet piezoelectric electric sensors, the coaxial piezoelectric cable 100 can be easily adjusted for cages of any size. Furthermore, the coaxial piezoelectric cable 100 can be configured into specialty shapes for increased sensitivity in predetermined areas without requiring custom manufacturing. Specialty shape configurations of the coaxial piezoelectric cable 100 can result in increased sensitivity over part or all of the cage area. The coaxial piezoelectric cable 100 may be more rugged than piezoelectric sheets. In stark contrast to the piezoelectric sheets, the coaxial piezoelectric cable 100 may be waterproof due to the insulative jacket 108. This waterproof nature can be important in rodent detection as the waterproof layers may protect the sensor from damage from rodent waste. For example, rodent waste could cause electrical damage to the piezoelectric sheet by short circuiting, corrosion damage by acids, mechanical damage from wear, etc. Thus, the waterproof layer (e.g. insulative jacket 108) of the coaxial piezoelectric cable 100 may reduce the need for additional external protection from rodent waste when placed in the cage 204 compared to using the piezoelectric film. Reducing the need for protection may allow configurations having close or direct contact between the rodent and the coaxial piezoelectric cable 100. Thus, increased sensitivity may be realized using the coaxial piezoelectric cable 100 as compared to other piezo-based sensors. The coaxial piezoelectric cable 100 may also be self-shielded and may be less susceptible to environmental interference and environmental vibrations.

However, one or both ends of the piezoelectric cable may not necessarily be waterproof due to limitations of the insulative jacket 108. Additionally, although the insulative jacket 108 may comprise rugged materials, such as Teflon, the rodent may chew through insulative jacket 108. In these embodiments, additional protection may be provided by a plastic film. The plastic film may prevent chewing and destruction of the piezoelectric cable 100 and may prevent exposure of the piezoelectric cable 100 to the rodent waste.

Figure 1B:
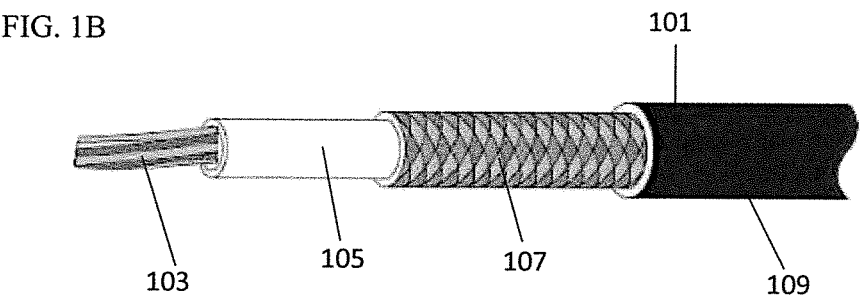
FIG. 1B depicts a diagram of an alternate coaxial piezoelectric cable in accordance with the principles of the present invention.

FIG. 1B depicts a diagram of an alternate piezoelectric coaxial cable 101 in accordance with the principles of the present invention. In this embodiment, insulative jacket 109 may be similar in all respects to insulative jacket 108. Conductive braid 107 may be similar in all respects to conductive braid 106. Conductive braid 107 may comprise a copper braid. Center core 103 may be similar in all respects to center core 102. Piezoelectric film 105 may be similar in all respects to piezoelectric film tape 104. In some embodiments, piezoelectric film tape 104 may comprise spiral wrapped piezoelectric film. Piezoelectric film 105 may comprise piezo copolymer. In these embodiments, piezoelectric film tape 104 may result in a more sensitive corresponding piezoelectric cable 100 than the piezoelectric cable 101 corresponding to the piezoelectric film 105. For example, piezoelectric cable 100 may have a capacitance of 980 pF/m whereas piezoelectric cable 101 may have a capacitance of 655 pF/m.

Figure 2:
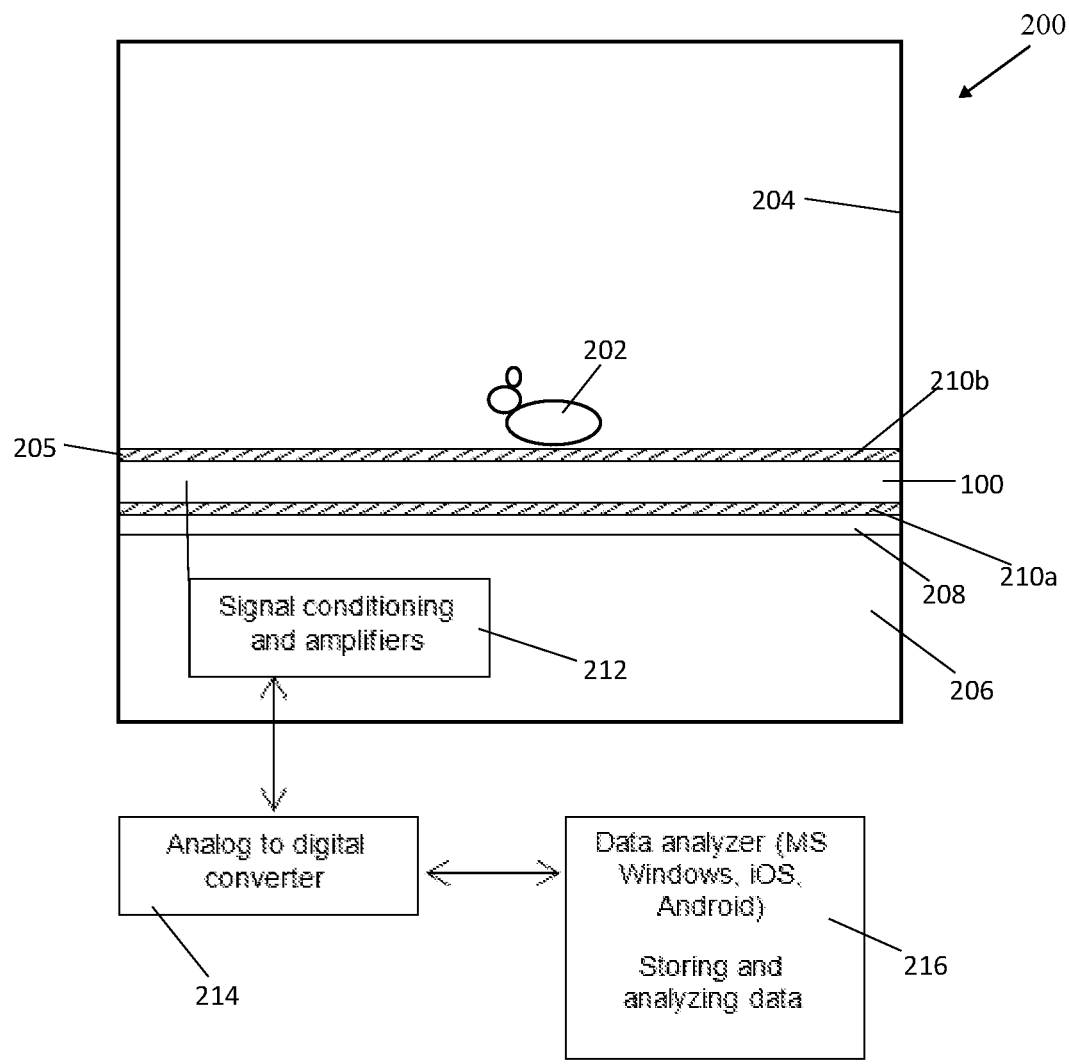
FIG. 2 depicts a block level diagram of a monitoring system using a coaxial piezoelectric cable in accordance with the principles of the present invention.

FIG. 2 depicts a block level diagram of a sleep and activity tracking system 200 for a rodent 202 using the coaxial piezoelectric cable 100 in accordance with the principles of the present invention. Some embodiments track sleep and activity of the rodent 202 using a single coaxial piezoelectric cable 100. For example, system 200 may comprise any live subject having movement that is capable of being measured with piezoelectricity. For example, the live subject may be rodent 202, or any other animal having a heartbeat, breath rate, etc. The live subject may be human or any animal useful as a human model for sleep, disease, disorder, impairment, or any other biological function. However, when detecting human movement, the piezoelectric cable 100 may be positioned under a pillow or mattress or embedded in a wearable clothing. In this embodiment, the wearable clothing may be non-binding such that the behavior patterns of the human are not altered.

The system 200 can include a cage 204 to confine the rodent 202. The cage 204 may be made of any material sufficient to contain the live subject, such as the rodent 202. Example materials include metal, plastics, acrylics, lexan, Plexiglas, glass, fiberglass, etc. Some embodiments use a transparent or translucent material for the cage 204 in order to allow for viewing of the rodent 202 from outside the cage 204. In accordance with the principles described, these materials may be formed into solid walls, slotted walls, lattices, wire frames, or any other pattern sufficient for retaining the animal. The cage 204 may comprise a floor 205 on which the animal may tread or rest, and can, for example, comprise a perimeter of three or more walls, if straight walls are used. Furthermore, the cage 204 may comprise one or more curved walls as long as a perimeter capable of retaining the animal is formed. A cage wall may comprise any shape that forms a perimeter and retains the animal within the bounds of the perimeter. In some embodiments, the cage 204 may comprise a plurality of vertical surfaces and may comprise one or more horizontal surfaces. In alternative embodiments, the cage 204 may comprise a plurality of vertical surfaces placed on a base, such as a rubber pad. In these embodiments, one or more plastic films may be situated between the cage 204 and the base. Furthermore, a plastic liner may be placed inside the cage 204 over the cage walls. The cage 204 may optionally have a lid, which may enclose the area above the perimeter that retains the animal. The lid may comprise a wire frame or other material similar to the remainder of the cage 204. The coaxial piezoelectric cable 100 may be placed anywhere in the vicinity of the live subject. In some embodiments, the coaxial piezoelectric cable can be sandwiched between two protective sheets of film or an be covered by a protective sheet once placed on a floor of the cage, for example. Any such films encasing the coaxial piezoelectric cable 100 may be made of plastic or other material.

In the embodiment depicted in FIG. 2, a piezoelectric coil assembly that includes the coaxial piezoelectric cable 100 positioned between the cage 204 and a base 206. A rubber pad 208 can be located between the piezoelectric coil assembly and the base 206. The piezoelectric coil assembly can comprise the coaxial piezoelectric cable 100 configured into a piezoelectric coil situated between plastic films 210a and 210b. The plastic films 210a and 210b may be configured to aid in retaining the shape and or position of the coaxial piezoelectric cable 100. The plastic films 210a and 210b may be thin such that interference with pressure sensitivity of the coaxial piezoelectric cable 100 is minimized or reduced. For example, if the cage 204 is a bottomless cage such that the film 210b also forms the floor 205 of the cage 204, the plastic films 210a and 210b may be sufficient to prevent the rodent 202 from chewing, biting, or otherwise tampering with the coaxial piezoelectric cable 100.

The plastic films 210a, 210b may comprise any material to retain the coaxial piezoelectric cable 100 in place and protect the coaxial piezoelectric cable 100 from damage by the live subject such as the rodent 202. Certain plastics may prevent the rodent 202 from damaging the coaxial piezoelectric cable 100 by chewing or scratching. By way of example, a plastic liner (not depicted) may also be placed over the walls and plastic film 210a, such that rodent waste, wood shavings, straw, etc. may be easily removed. The plastic liner and any shavings and straw may be easily replaced for the rodent's comfort and/or health.

The coaxial piezoelectric cable 100 may be placed on the plastic film 210a or the coaxial piezoelectric cable 100 may be configured into a piezoelectric coil assembly as described above. The configuration of the coaxial piezoelectric cable may comprise any coil. As used herein, "coil" means any of a serpentine layout (serpentine shape, such as switchbacks) spirals, shaped spirals, circular spirals, rectangular spirals, square spirals, combination serpentine and spiral layouts, three-dimensional spirals such as conical spirals, springs, etc.

The base 206 may comprise any material sufficient to withstand the weight of the rodent 202, or other live subject. Examples include plastics, rubber, vinyl, etc. A perimeter of the base 206 may be substantially similar in size to that of a bottom of the cage 204.

The rubber pad 208 may be placed on the base 206. The rubber pad 208 may comprise any material sufficient for noise reduction of the signal produced by the coaxial piezoelectric cable 100. For example, human foot traffic may cause vibrations in a laboratory room's floor that can be transmitted to the coaxial piezoelectric cable 100. Materials, such as rubber and vibration dampening plastics, may aid in reducing signal noise from environmental vibrations.

The coaxial piezoelectric cable 100 may be connected to a signal conditioner and amplifier 212 through a wired or wireless connection. The signal conditional and amplifier 212 may then amplify the received electrical signals to generate an amplified signal. The amplified signal may then be transmitted to an analog to digital converter (ADC) 214, which may be onboard or separate from the signal conditioner and amplifier 212. The ADC 214 may convert the amplified analog signal to a digital signal. The ADC 214 may then feed the digital signal to a computer system 216 running data acquisition and analysis software. For example, the computer system 216 may operate on MICROSOFT WINDOWS, OSX, ANDROID, iOS, LINUX, UNIX, or any other operating system capable of data storage and operating corresponding data acquisition software. The data acquisition software may receive and/or store the data. In some embodiments, the data acquisition software can simultaneously analyze the data to classify it into various behaviors, such as "active," "inactive," "sleep," "wake," "dead," "sick," "rapid-eye-movement (rem) sleep," "non-rem sleep," etc.

The coaxial piezoelectric cable 100 may output an analog signal comprising a continuous waveform, rather than discrete digital representations of magnitude. Thus, the ADC 214 may convert the analog voltage signal corresponding to pressure change, or mechanical stress, on the coaxial piezoelectric cable 100 to discrete digital values. In some embodiments, the signal of the piezoelectric cable 100 may correspond to charge, measured in units of capacitance/meter. In further embodiments, the coaxial piezoelectric cable 100 outputs voltage levels in the range of tens to hundreds of microvolts ($\mu Vs$). After amplification, the signal range may be between +10 V to −10 V, depending on hardware limitations. Rats may be heavier than mice at a ratio of about eight or nine to one. For example, the mass of a rat may be 170 g, whereas the mass of a mouse may be 20 g. Furthermore, the mass of a baby mouse may be 15 g. In embodiments wherein the rodent comprises a rat, the signal may be amplified to about 0V-5V. In embodiments wherein the rodent comprises a mouse, the signal may also be amplified by a secondary gain, due to the lighter mass of the mouse, to between about −5V to +5V. The combination of the signal conditioner and amplifier 212 and ADC 214 are capable of producing a digitized signal that can be acquired by the data analyzer components of the computer system 216.

One of ordinary skill will recognize that other data acquisition techniques can be utilized to sensed movement information of the rodent, such as 4-20 mA loop sensor technology typically employed in industrial environments.

Thus, the signal conditioner and amplifier 212 may receive a signal representative of raw voltages from the coaxial piezoelectric cable 100. This signal may require amplification in order for the ADC 214 and/or data analyzer 216 to process the signal into corresponding piezoelectric data. As mentioned above, for example, embodiments include a coaxial piezoelectric cable 100 that outputs an analog signal between 0 to 5V, −5 to +5V, and/or −10 to +10V depending on the mass of the rodent and amplification used. Thus, the signal conditioner and amplifier 212 and/or ADC 214 may amplify the analog signal from the coaxial piezoelectric cable 100. Furthermore, the signal conditioner and amplifier 212 and/or ADC 214 may provide smoothing of the signal and/or filtering to reduce or remove signal noise before converting the signal into representative digital values.

The analog to digital converter 214 may comprise a standalone device or part of the signal conditioner and amplifier 212 or data analyzer 216. In an embodiment in which the signal conditioner and amplifier 212 is not utilized, the ADC 214 may convert the raw voltage signal received from coaxial piezoelectric cable 100 into a digitized signal to be used by the data analyzer computer system.

The data analyzer computer system 216 will be described further with respect to FIG. 14.

Figure 3A:
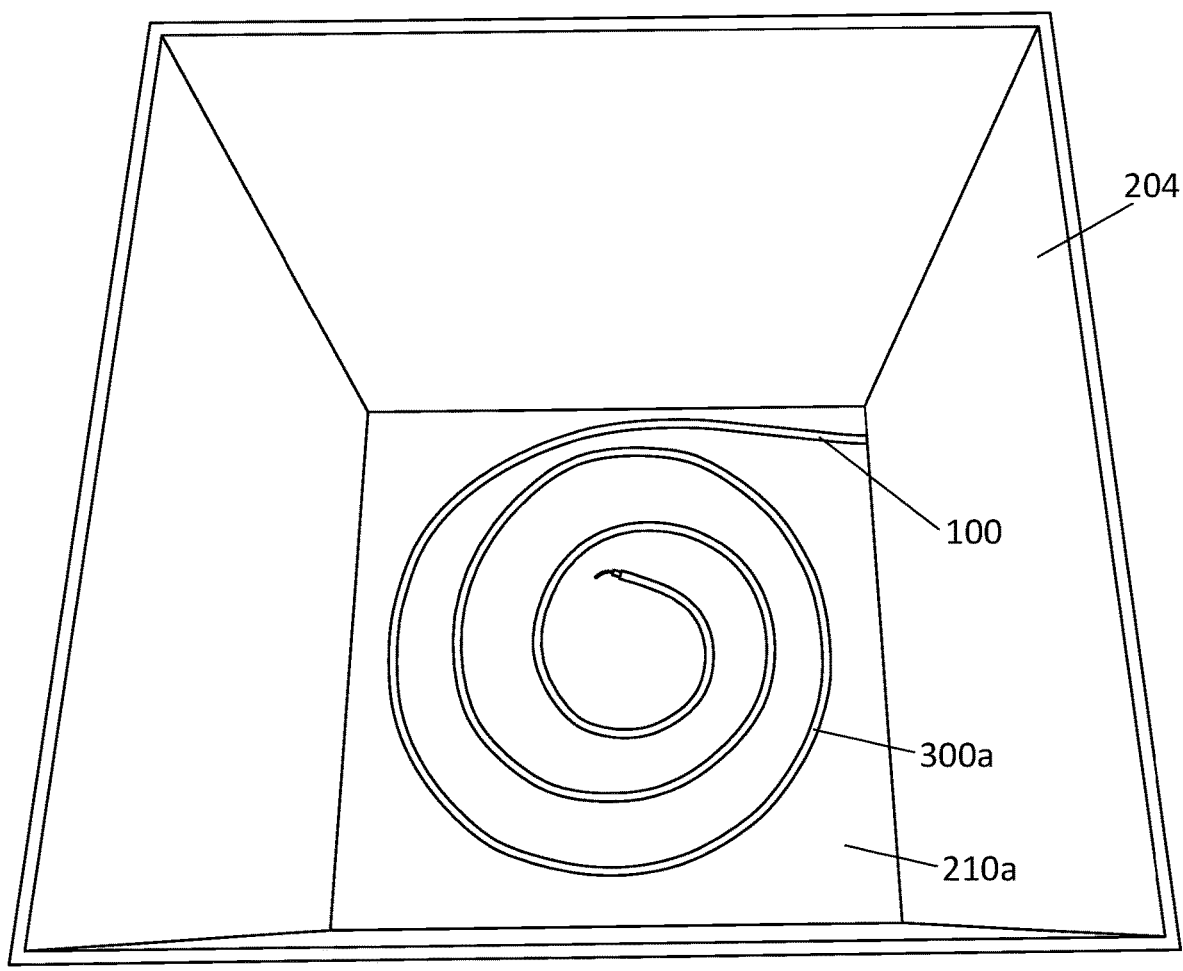
FIGS. 3A-3E depict diagrams of a top-down view into the cage of FIG. 2 with the coaxial piezoelectric cable configured in various arrangements in accordance with the principles of the present invention.

FIG. 3A depicts a diagram of an unobstructed top-down view into the cage 204 of FIG. 2 with the coaxial piezoelectric cable 100 configured in a circular spiral coil 300a in accordance with the principles of the present invention. In some embodiments the coaxial piezoelectric cable 100 may be positioned at or near the bottom of the cage 204. The coaxial piezoelectric cable 100 may simply be positioned below the rodent 202. Further embodiments include the coaxial piezoelectric cable 100 positioned to receive pressure from the weight of the rodent 202. Example embodiments include placing the bottom of cage 204 over the coaxial piezoelectric cable 100, wherein the coaxial piezoelectric cable 100 is outside the cage 204. As mentioned above, use of a bottomless cage 204 is envisioned as well within the scope of the present invention.

For example, the coaxial piezoelectric cable 100 may be configured into a serpentine/spiral coil, wherein the serpentine/spiral shape comprises a combination spiral and/or serpentine switchback. The spiral may be equiangular or non-equiangular. Furthermore, the spiral may be centered or off-center, based on the desired focal point within the cage 204 of where sensing by the coaxial piezoelectric cable 100 is desirable. The switchbacks may have equal length, or increasing or decreasing length. The spacing between neighboring sections of the coaxial piezoelectric cable 100 may be set to achieve a predetermined sensitivity.

In some embodiments, additional noise cancellation is desired. For example, noise cancellation may be desired in embodiments wherein the cage 204 houses one rodent 202 or multiple rodents. A secondary coaxial piezoelectric cable (not shown) may be placed in the vicinity of the cage 204 (inside or outside). The secondary coaxial piezoelectric cable can act as a reference noise input to aid in adaptive noise cancellation. In cages housing more than one animal, multiple coaxial piezoelectric cables can be used to isolate the signals from individual animals using statistical and computational techniques such as Independent component analysis (ICA).

The coaxial piezoelectric cable 100 of the system 200 can be folded into any shape and can be placed anywhere in the vicinity of the cage 204 and is not limited to the position and shape of the cable as depicted in FIGS. 3A-3E. As an example, the coaxial piezoelectric cable 100 can be 2.7 mm in diameter. The coaxial piezoelectric cable 100 can be about 94.0 cm long with a capacitance of about 860 pF. In addition to the planar shape, there may be a three-dimensional (3D) shape to ensure contact to the cage which may have a slight bow shape. For example, instead of a simple spiral as depicted in FIG. 3A we have a conical shape to ensure full contact to cage bottom if the cage bottom has concave shape. For example, some cage bottoms may be bowed, and therefore all parts of the cage bottom may not adequately contact the coaxial piezoelectric cable 100 for accurate measurement. Therefore, a three-dimensional coil shape of piezoelectric cable may be useful to ensure positive, or more extensive, contact with the bottom of the cage.

Figure 3B:
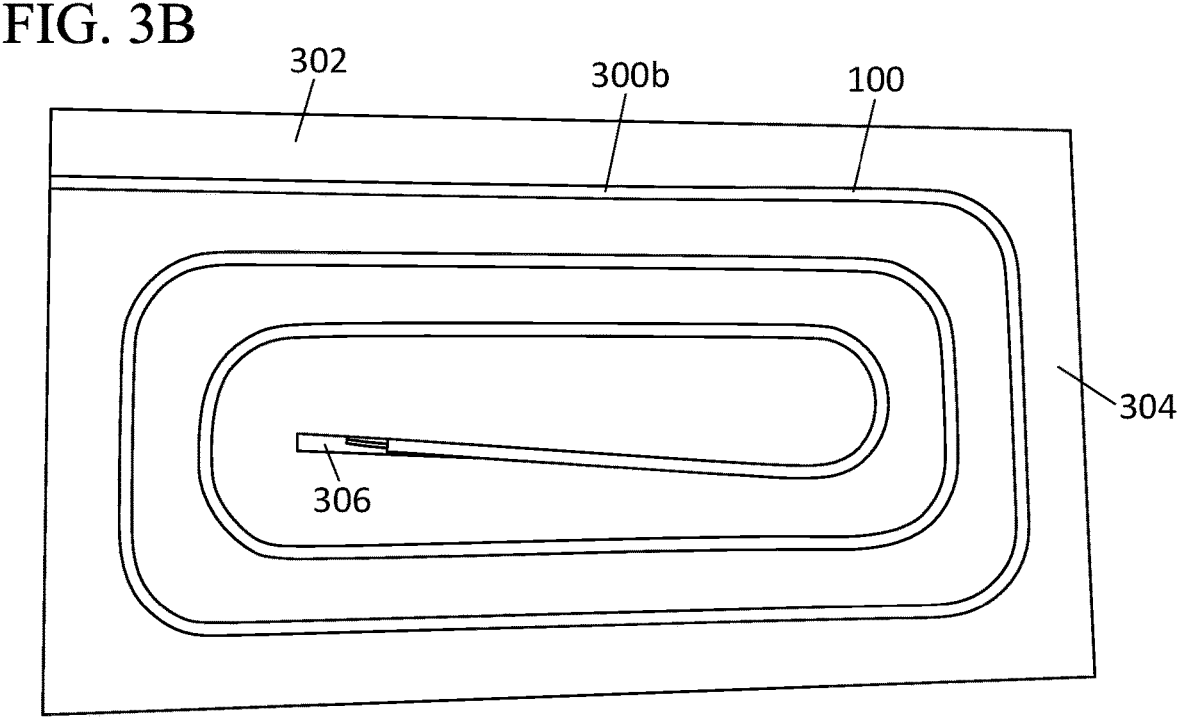

FIG. 3B depicts a diagram of an unobstructed top-down view into the cage 204 of FIG. 2 with the coaxial piezoelectric cable 100 configured in a rectangular spiral coil 300b in accordance with the principles of the present invention. In some embodiments, the coaxial piezoelectric cable 100 may be rigid, such as when coated by Polytetrafluoroethylene (e.g. Teflon). The rigid embodiments of the coaxial piezoelectric cable 100 may be biased to an unbent configuration. Therefore, these embodiments may be held into shape by a retainer 302.

For example, the retainer 302 may comprise a base 304. The base 304 may comprise a substantially planar surface. However, the base 304 may be configured to receive the coaxial piezoelectric cable 100. For example, the base 304 may extend to the substantially planar surface. However, the base 304 may be receded from the substantially planar surface in the form of a trench 306. The base 304 may be configured to receive the coaxial piezoelectric cable 100 by frictional fit of the coaxial piezoelectric cable 100 with the trench 306. The trench 306 may be shaped in a coil (e.g. rectangular spiral coil 300*b*). Thus, the retainer 302 may hold the coaxial piezoelectric cable 100 in the coil form when frictional fit with the retainer 302.

Furthermore, the trench 306 may be sufficiently shallow such that at least part of the diameter of the coaxial piezoelectric cable 100 extends beyond the substantially planar surface of the base 304. In this manner, the coaxial piezoelectric cable 100 may detect rodent movement when frictionally fit with the base 304 and placed within or under the cage 204.

Figure 3C:
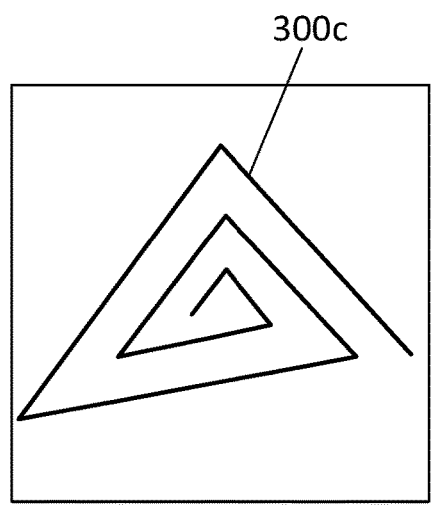

FIG. 3C depicts a diagram of a top-down view into the cage 204 of FIG. 2 with the coaxial piezoelectric cable 100 uncovered and configured in a triangular spiral coil 300*c* in accordance with the principles of the present invention.

Figure 3D:
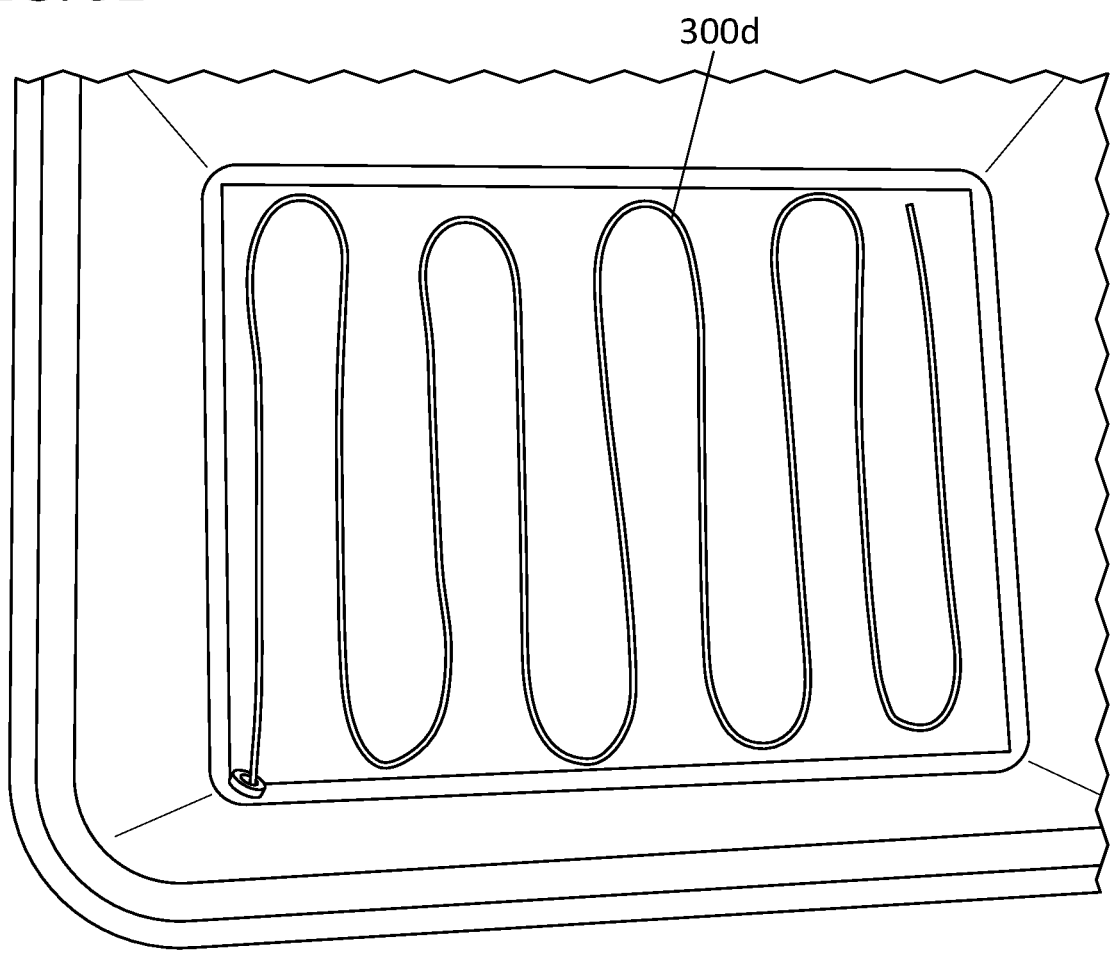

FIG. 3D depicts a diagram of a top-down view into the cage 204 of FIG. 2 with the coaxial piezoelectric cable 100 uncovered and configured in a serpentine switchback coil 300*d* in accordance with the principles of the present invention. As depicted, each run of the switchback may be equal in length. Embodiments include switchbacks wherein the runs are not equal in length. For example, the length can be increase, decreasing, varied, etc.

Figure 3E:
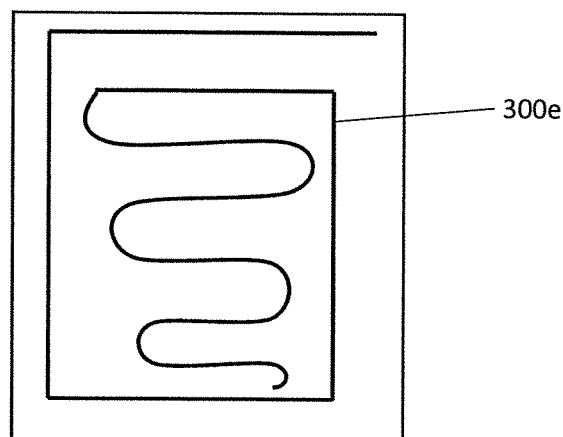

FIG. 3E depicts a diagram of a top-down view into the cage 204 of FIG. 2 with the coaxial piezoelectric cable 100 uncovered and configured in a combined spiral and serpentine switchback 300*e* in accordance with the principles of the present invention. This example includes a spiral around a serpentine switchback. Other examples include the serpentine switchback outside the spiral. The configuration of the coaxial piezoelectric cable 100 may be adapted to achieve heightened sensitivity in one or more areas.

Figure 3F:
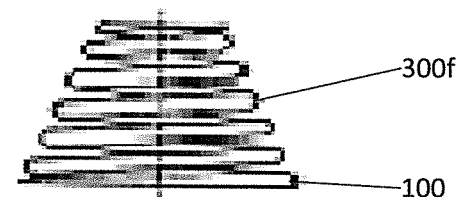
FIGS. 3F-3J depict diagrams of a view of the coaxial piezoelectric cable of FIG. 1 configured in a three-dimensional coil for rodent detection in accordance with the principles of the present invention.

FIG. 3F depicts a diagram of a view of the coaxial piezoelectric cable 100 configured in a conical spring coil 300*f* in accordance with the principles of the present invention. Thus, embodiments of the coaxial piezoelectric cable 100 may be configured in a three-dimensional coil for detection of rodent movement. This may be used, for example, when the bottom of the cage 204 is bowed, concave, convex, etc. In some embodiments, the conical spring coil 300*f* may be placed on an end. In other embodiments, the conical spring coil 300*f* may be placed on a side.

Figure 3G:
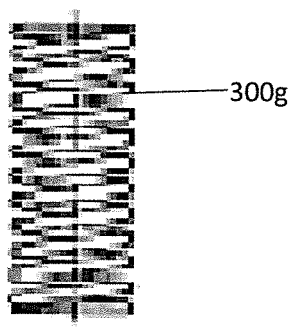

FIG. 3G depicts a diagram of a view of the coaxial piezoelectric cable 100 configured in a constant pitch spring coil 300*g*. The constant pitch spring coil 300*g* may be positioned on an end or on a side for rodent detection.

Figure 3H:
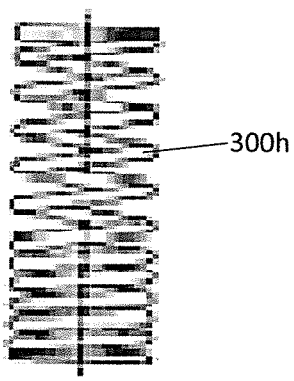

FIG. 3H depicts a diagram of a view of the coaxial piezoelectric cable 100 configured in a variable pitch spring coil 300*h* in accordance with the principles of the present invention. The variable pitch spring coil 300*h* may be placed on an end or a side for rodent detection.

Figure 3I:
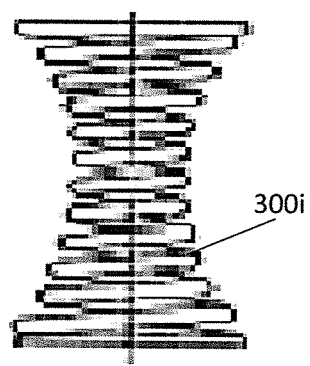

FIG. 3I depicts a diagram of a view of the coaxial piezoelectric cable 100 configured in an hourglass spring coil 300*i* in accordance with the principles of the present invention. The hourglass spring coil 300*i* may be positioned on an end or a side for rodent detection.

Figure 3J:
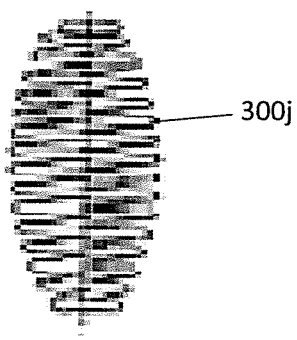

FIG. 3J depicts a diagram of a view of the coaxial piezoelectric cable 100 configured in a barrel spring coil 300*j* in accordance with the principles of the present invention. The barrel spring coil 300*j* may be positioned on an end or a side for rodent detection.

Figure 3K:
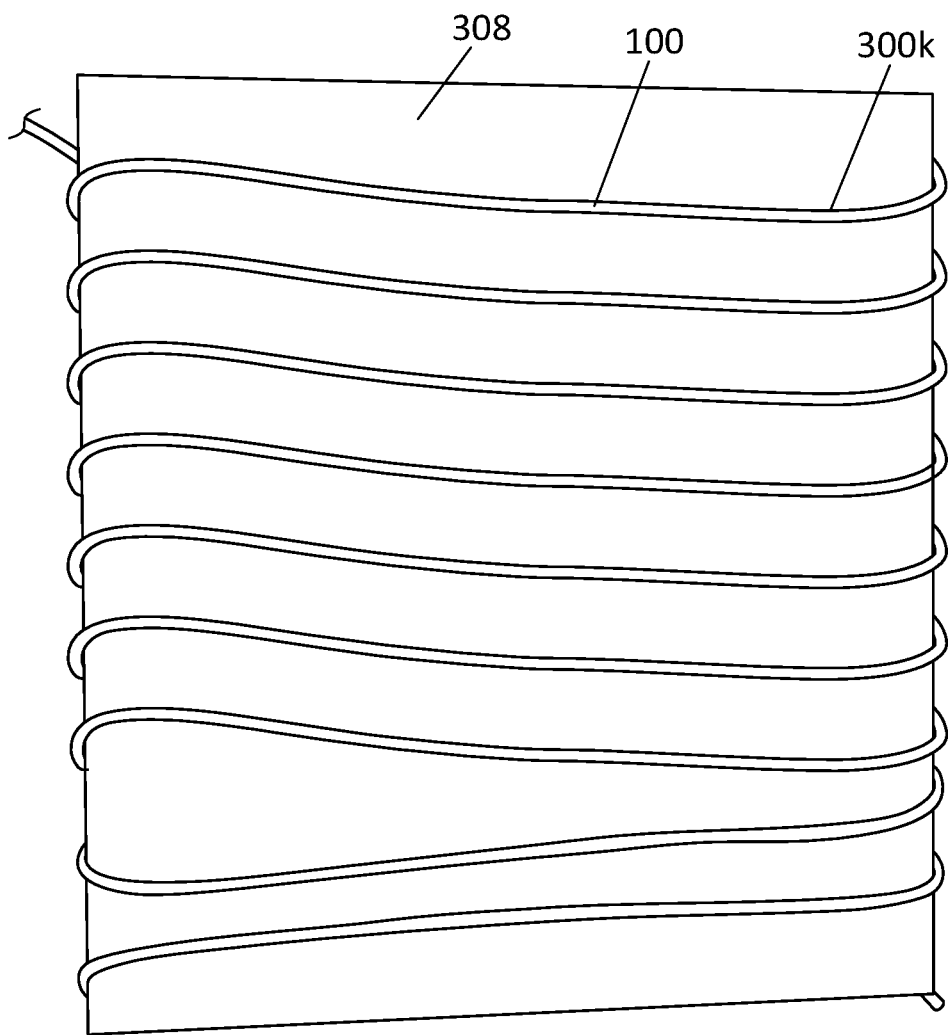
FIGS. 3K-3M depict diagrams of a view of the coaxial piezoelectric cable of FIG. 1 configured in a three-dimensional coil around a retainer for rodent detection in accordance with the principles of the present invention.

FIG. 3K depicts a diagram of a view of the coaxial piezoelectric cable 100 configured in a spring coil 300*k* around a retainer 308 in accordance with the principles of the present invention. Retainer 308 may be used to support the three-dimensional shape of the coil 300*k*. In some embodiments, the retainer 308 may be similar in all respects to retainer 304. Furthermore, a trench of the retainer 308 may span multiple surfaces of the retainer 308.

Figure 3L:
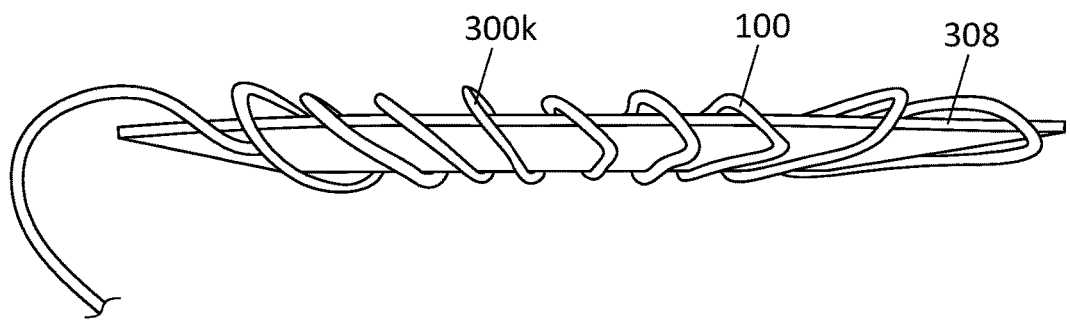
Figure 3M:
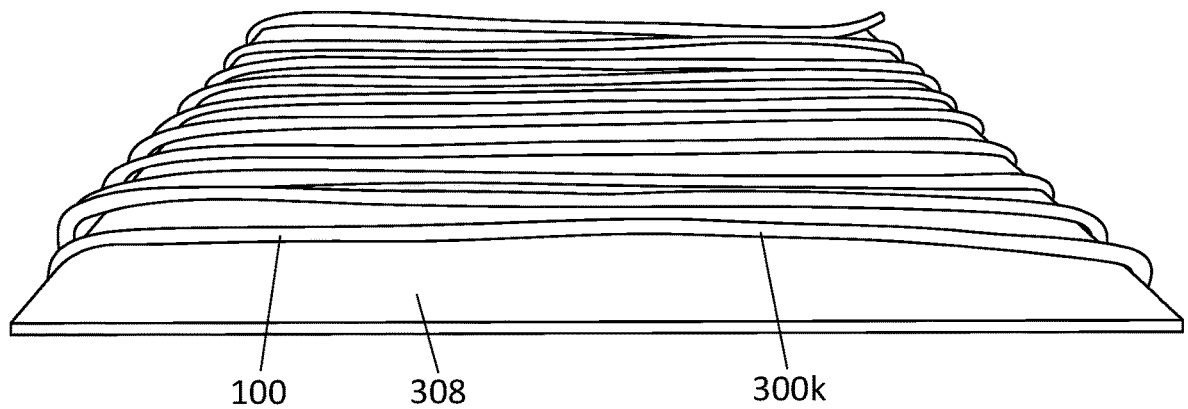

FIG. 3L depicts a diagram of a side view of the coaxial piezoelectric cable 100 configured in the spring coil 300*k* around a retainer 308 in accordance with the principles of the present invention FIG. 3M depicts a diagram of an alternate view of the coaxial piezoelectric cable 100 configured in the spring coil 300*k* around a retainer 308 in accordance with the principles of the present invention.

Figure 3N:
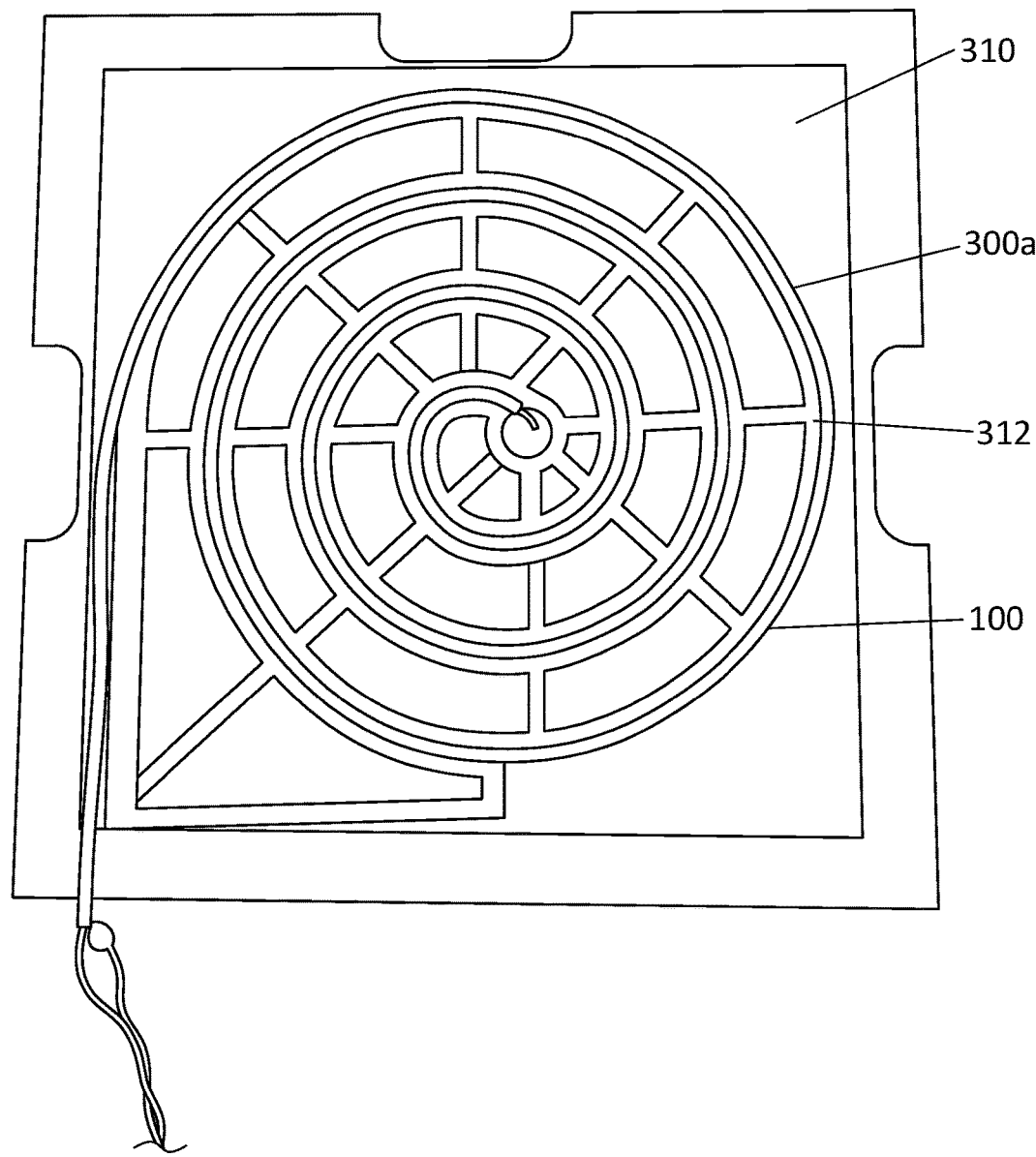
FIG. 3N depicts a diagram of a view of the coaxial piezoelectric cable configured in the circular spiral coil of FIG. 3A frictional fit with a retainer in accordance with the principles of the present invention.

FIG. 3N depicts a diagram of a view of the coaxial piezoelectric cable 100 configured in the circular spiral coil of FIG. 3A frictional fit with a retainer 310. The retainer 310 may hold the piezoelectric cable 100 in a circular spiral 300*a*. For example, the retainer 310 may comprise supports 312 extending from the surface of retainer 310 such as, for example, to form a groove or channel. Piezoelectric cable 100 may frictionally fit between supports 312. Furthermore, a sleeve (not depicted) may be placed over the retainer 310 such that the rodent may be provided a smooth surface that does not necessarily interfere with activity. The sleeve may be supported by the piezoelectric coil 100 such that movement on the sleeve transfers to the piezoelectric cable 100.

Figure 4A:
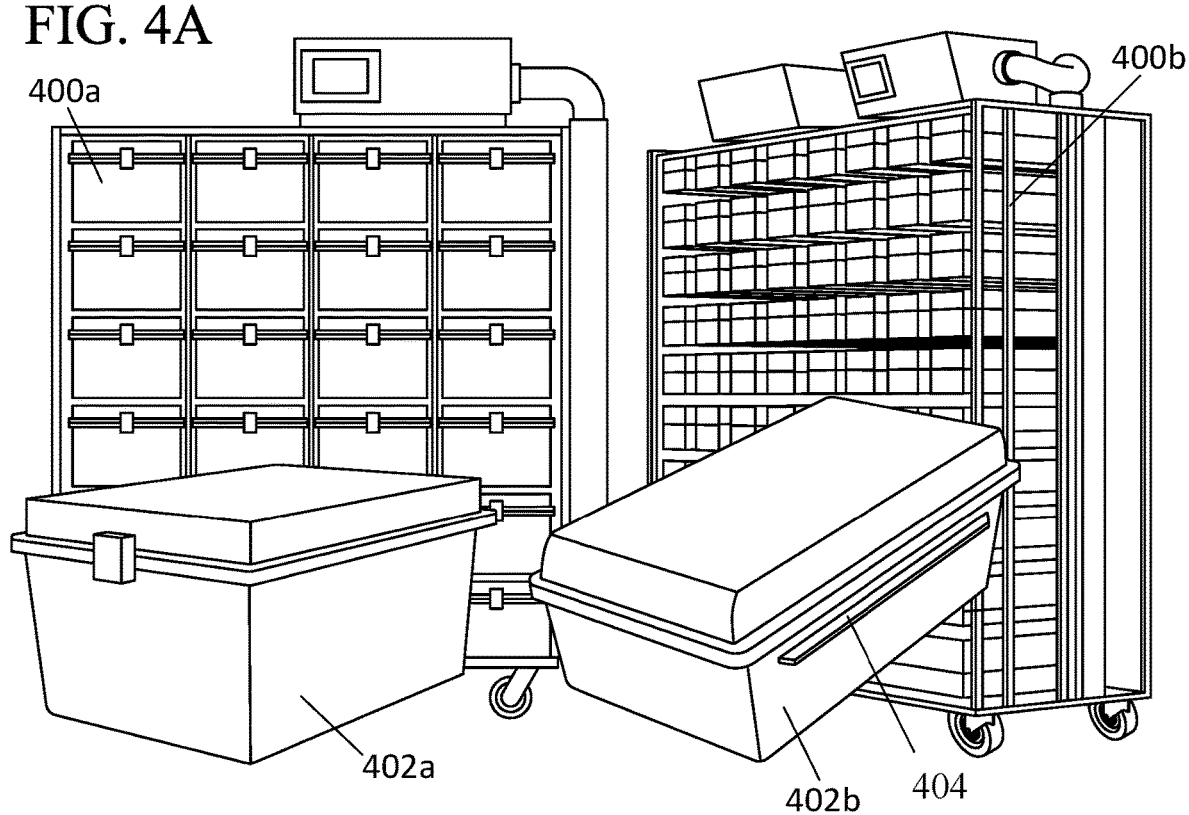
FIG. 4A depicts example rack systems in accordance with the principles of the present invention.

FIG. 4A depicts example rack systems 400*a* and 400*b* in accordance with the principles of the present invention. Rack systems 400*a* and 400*b* may comprise one or more cages 402*a*, 402*b*, respectively. Each cage 402*a*, 402*b* may correspond to one or more respective coaxial piezoelectric cables 100. Thus, movement may be detected in each respective cage 402*a*, 402*b*. In some embodiments, the cage 402*a* may be supported on the rack 400*a* by the bottom of the cage 402*a*. In other embodiments, the cage 402*b* may be supported by rails 404 that suspend the cage 402*b* on the rack 400*b*.

Figure 4B:
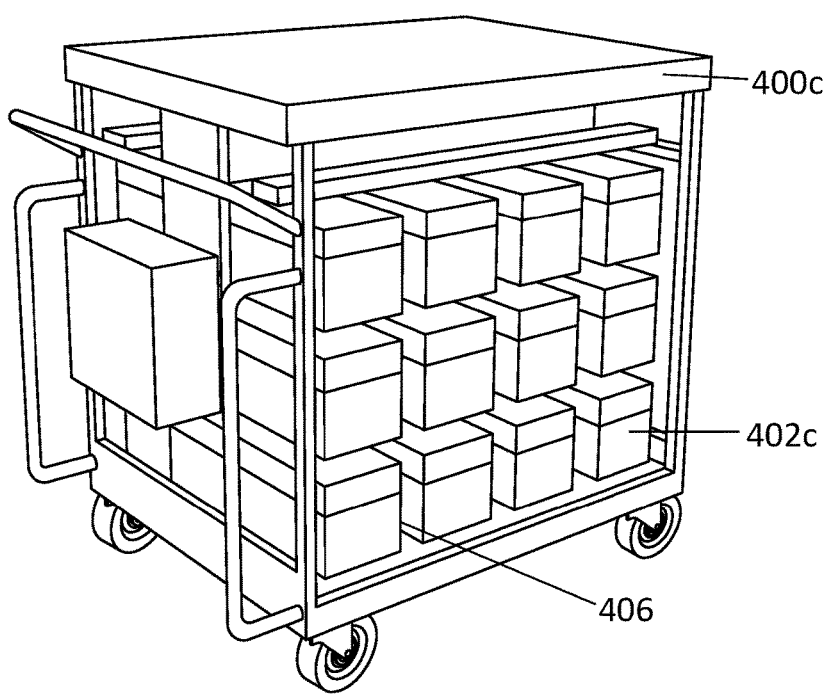
FIG. 4B depicts an example rack in which the cages are supported by a cross beam underneath each cage and guided by rails similar to rails (but not easily discernable in FIG. 4B) in accordance with the principles of the present invention.

FIG. 4B depicts an example rack 400*c* in which a cage 402*c* is supported by a cross beam 406 underneath each cage 402*c* and guided by rails similar to rails 404 (but not easily discernable in FIG. 4B) in accordance with the principles of the present invention. The coaxial piezoelectric cable 100 may be positioned under or near one or more of the rails. Alternatively, the coaxial piezoelectric cable 100 may be positioned between the cross beam 406 and the cage 402*c*, or otherwise near the cross beam 406 wherein movement of the rodent 202 is detectable.

The monitoring system described herein can be adapted to any of these rack systems by integrating one or more coaxial piezoelectric cables as part of the track and/or ridges of the rack system for each cage housed within a particular rack system. In such arrangement, the full or partial weight of each cage (e.g., 204, 402*a*, 402*b*, 402*c*) may rest on one or more associated coaxial piezoelectric cable 100. Thus, animal motion within the cage 204, 402*a*, 402*b*, 402*c* may be transferred to the associated one or more coaxial piezoelectric cable 100. Individual cages 204, 402*a*, 402*b*, 402*c* can be removed and replaced without being encumbered by cables and/or sensors. One, two, or more independent coaxial piezoelectric cables can be used and/or integrated in the track for single or multiple animal sensing.

As can be seen, each rack may comprise a plurality of cages 204, 402*a*, 402*b*, 402*c*. Each cage 204, 402*a*, 402*b* may enclose one or more live subjects. Each cage 204, 402*a*, 402b, 402c may be positioned relative to one or more corresponding coaxial piezoelectric cables 100a, 100b, such that one or more respective piezoelectric signals may be received corresponding to each respective cage 204, 402a, 402b, 402c. Thus, the signal conditioner and amplifier 212 may process multiple respective piezoelectric signals. The ADC 214 may convert multiple respective piezoelectric signals. Furthermore, the data analyzer computer system 216 may receive the respective piezoelectric signals and may determine the classification of multiple respective states corresponding to the respective live subject(s) of each cage 204, 402a, 402b, 402c.

Figure 4C:
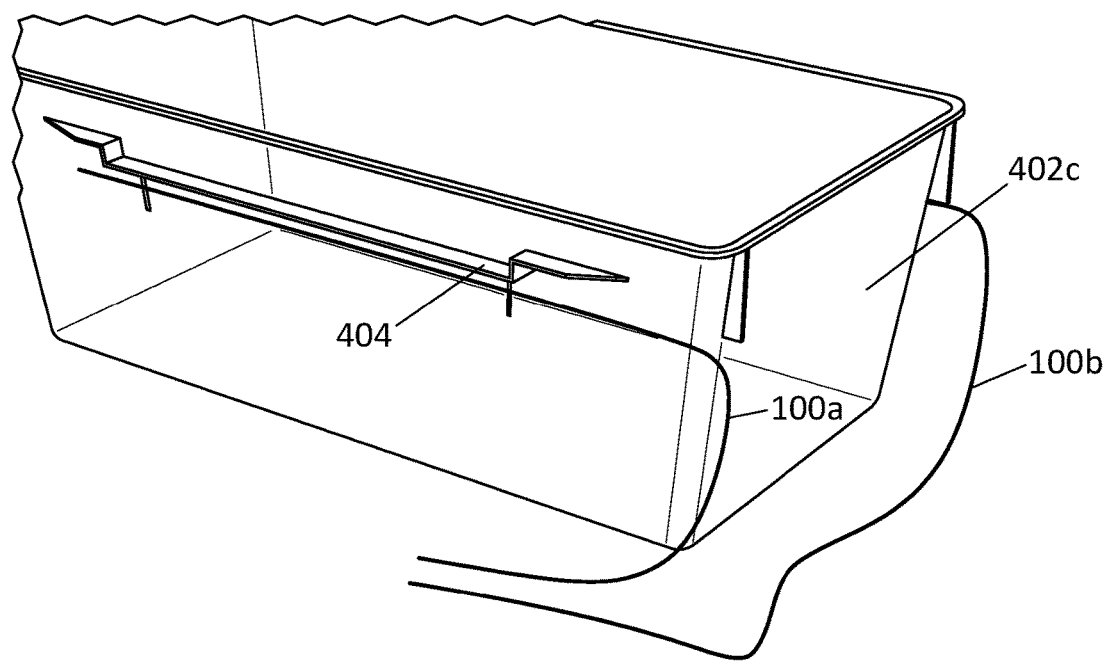
FIG. 4C depicts a cage comprising rails in accordance with the principles of the present invention.

FIG. 4C depicts the cage 402c comprising one or more rails 404 in accordance with the principles of the present invention. In this embodiment, multiple coaxial piezoelectric cables 100a and 100b may be present for detection of the rodent 202 in accordance with the principles of the present invention. The coaxial piezoelectric cables 100a and 100b may be positioned under each of the respective rails 404 such that motion (including breathing and heartbeat in some embodiments) may be detected. For example, the coaxial piezoelectric cables 100a and 100b may support the rails 404 that, in turn, support the weight of the cage 402c. In other embodiments, the weight of the cage 402c may be supported at the bottom of the cage 402c and the rails 404 may simply exert pressure on the coaxial piezoelectric cables 100a and 100b when movement occurs due to compression against further supports under each coaxial piezoelectric cable (depicted in a later diagram). In other embodiments, the coaxial piezoelectric cables 100a and 100b may be suspended via tracks in the frame of the rack and/or ridges in the cage 402c such that movement of the rodent 202 may be detected.

Figure 4D:
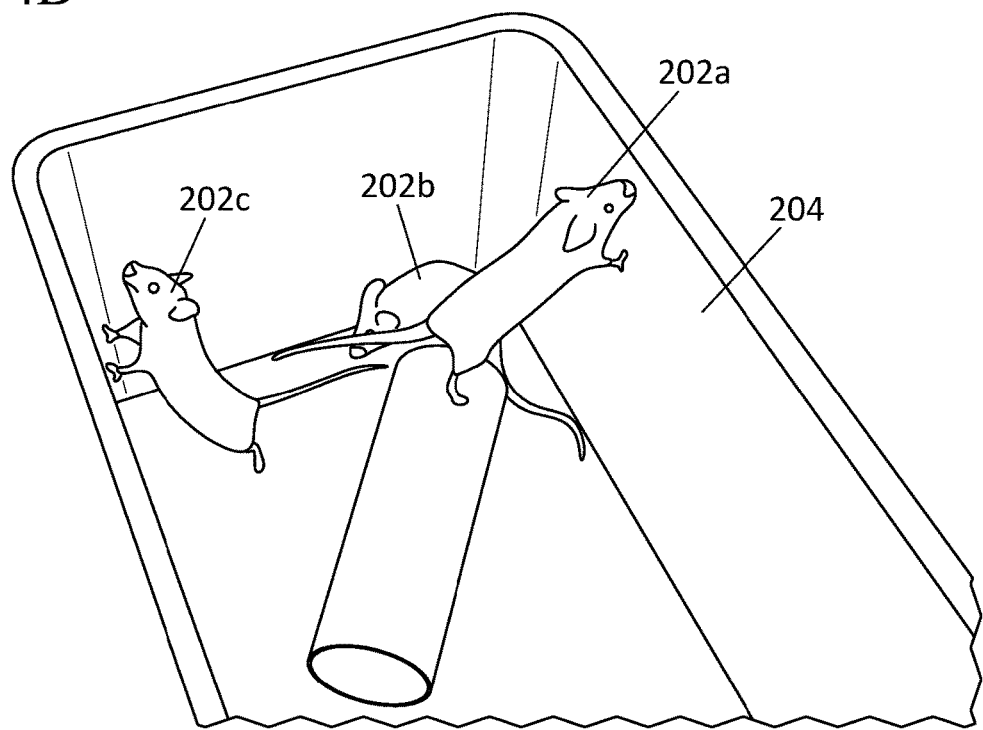
FIG. 4D depicts a cage having multiple rodents in accordance with the principles of the present invention.

FIG. 4D depicts the cage 204 having multiple rodents 202a, 202b, and 202c in accordance with the principles of the present invention. Each rodent 202a, 202b, 202c generates a respective signal based on its individual movements. Therefore, noise cancellation may be desirable in such embodiments. As described above, multiple coaxial piezoelectric cables can be used to isolate the signals from individual animals using statistical and computational techniques such as Independent component analysis (ICA).

Figure 5A:
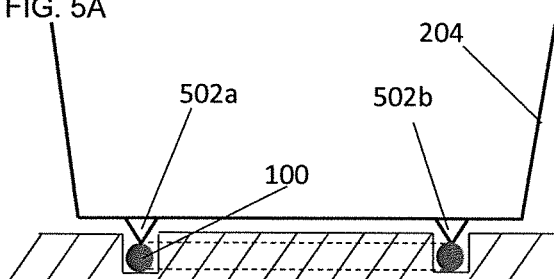
FIG. 5A depicts a cage resting on a single coaxial piezoelectric cable configured in a U-shape under the bottom ridges of the cage in accordance with the principles of the present invention.

FIG. 5A depicts the cage 204 resting on a single coaxial piezoelectric cable 100 configured in a U-shape under the bottom ridges 502a of the cage 204 in accordance with the principles of the present invention. The ridges 502a may act as points to concentrate force on a relatively small area to create high pressure (Pressure=Force/Area), effectively amplifying detectable movement of the rodent 202 within the cage 204.

Figure 5B:
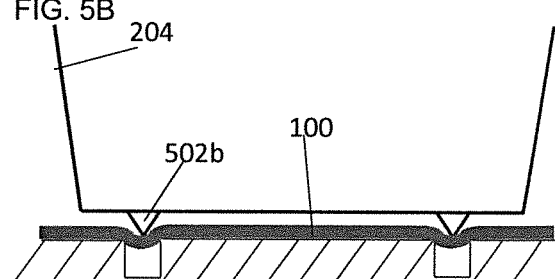
FIG. 5B depicts a cage resting on one U-shaped coaxial piezoelectric cable lying perpendicular to the cages ridges in accordance with the principles of the present invention.

FIG. 5B depicts the cage 204 resting on one U-shaped coaxial piezoelectric cable 100 lying perpendicular to the cages ridges 502b in accordance with the principles of the present invention.

Figure 5C:
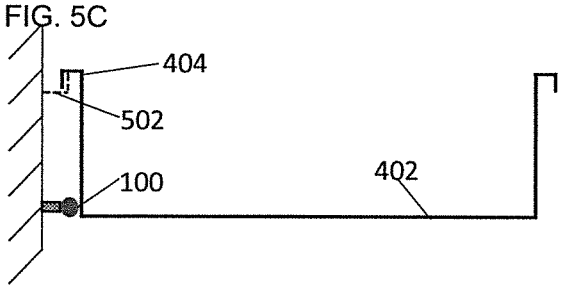
FIG. 5C depicts a cage pivotally resting on rail at the top and against coaxial piezoelectric cable at the bottom side such that movement by the rodent within cage causes pressure against coaxial piezoelectric cable in accordance with the principles of the present invention.

FIG. 5C depicts the cage (e.g., 402b) with a top rail pivotally resting on a support portion 502 of a rack system. A bottom portion of the cage 402b rests against the coaxial piezoelectric cable 100 such that movement by the rodent 202 within the cage 402b causes pressure against the coaxial piezoelectric cable 100 in accordance with the principles of the present invention.

Figure 5D:
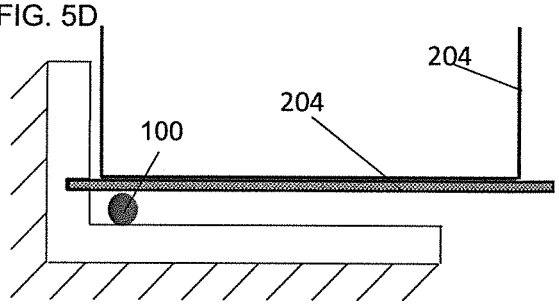
FIG. 5D depicts a cage resting on a cantilever such that movement of the cage causes movement of the cantilever, thereby causing pressure on the piezoelectric cable in accordance with the principles of the present invention.

FIG. 5D depicts the cage 204 resting on a cantilevered support 506 such that movement of the cage 204 (i.e., movement of the rodent 202 within the cage 204) causes movement of the cantilevered support 506, thereby causing pressure on the coaxial piezoelectric cable 100 in accordance with the principles of the present invention. In some embodiments the coaxial piezoelectric cable 100 may be positioned proximate to and below a fulcrum end of the cantilevered support. In other embodiments, the coaxial piezoelectric cable may be positioned proximate to an end opposite of the fulcrum end of the cantilevered support.

Figure 5E:
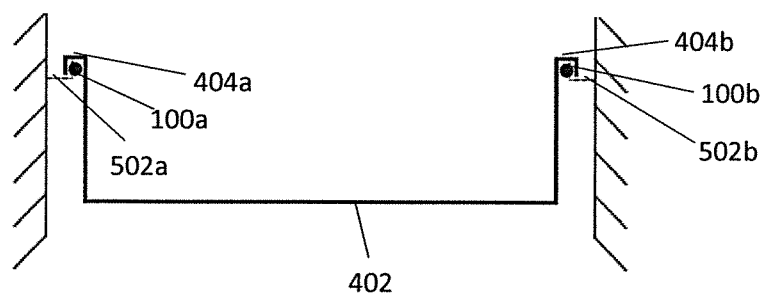
FIG. 5E depicts a cage supported by rails, wherein the coaxial piezoelectric cables are positioned between the rails and the respective supports in accordance with the principles of the present invention.

FIG. 5E depicts the cage 204 supported by rails 404a and 404b, wherein the coaxial piezoelectric cables 100a and 100b are positioned between the rails 404a and 404b and the respective supports 502a and 502b of a rack system in accordance with the principles of the present invention.

As described above, the signal measuring the potential difference between the copper braid and inner core of the coaxial piezoelectric cable 100 may be filtered and/or amplified using the signal conditioner and amplifier 212 and the ADC 214 before being provided to the data analyzer computer system 216 which comprises data acquisition software. The acquisition software may, in real time, filter the data and extract a set of features (periodically) from the data received by the data analyzer computer system 216. The software may apply a statistical method to classify the received data into classes or events. Examples includes "Active/Inactive," "Sleep/Wake," "Dead/Alive," "Sick/Well," "Rem/Non-rem," etc. The acquisition software can store the received data and the extracted features on the hard disk of the data analyzer computer system 216. Post collection of data, additional analysis software can extract the set of features stored by the acquisition software and apply more sophisticated (and computationally heavy) statistical methods for a more accurate classification of the received and processed data into the classes or events.

Figure 6:
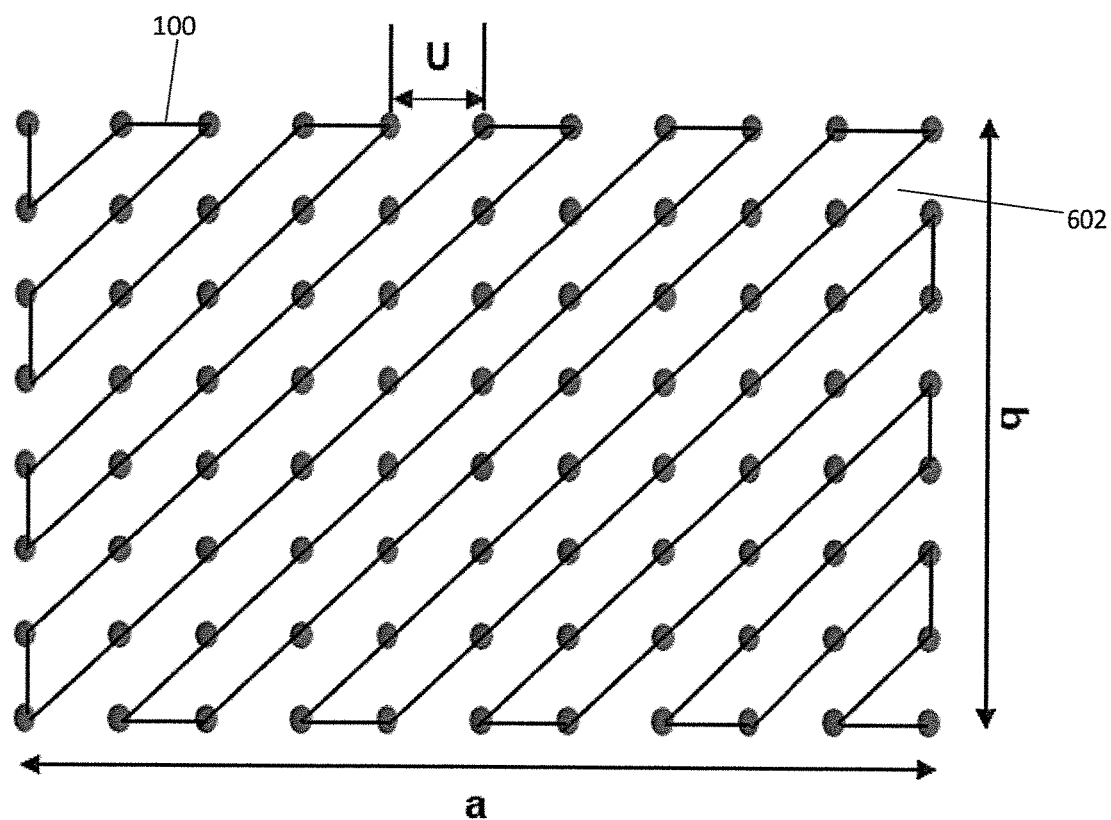
FIG. 6 depicts a model for determining the length of coaxial piezoelectric cable needed for a given cage floor for uniform detection of a live subject of a predetermined size in accordance with the principles of the present invention.

FIG. 6 depicts a model for determining the length of coaxial piezoelectric cable 100 needed for a given cage floor 602 for uniform detection of a live subject of a predetermined size in accordance with the principles of the present invention. In this embodiment, the coaxial piezoelectric cable 100 is spaced evenly on the cage floor 602. The variable "a" represents the length of the cage floor, the variable "b" represents the width of the cage floor, the variable "U" represents the size of the live subject. The length, "P," can be determined as follows.

$$L = \frac{a}{U}, B = \frac{b}{U}, \text{where } \{L, B \in \mathbb{Z} \mid L, B > 0\} \quad \text{Equation [1]}$$

$$P = (L+B) + \left(\sqrt{2} * B * (L-B+1)\right) + \left(2 * \sqrt{2} * \left(\sum_{K=1}^{B-1} B - k\right)\right), \text{ for } L \geq B \quad \text{Equation [2]}$$

Various alternatives for calculating a value for "u" can be utilized without departing from the scope of the present invention. The size may be an average expected size for the particular live subject that is being monitored. For a rodent, the value "u" may represent the distance along the torso between the shoulders and hips of the rodent. The value "u" may be the distance from the nose of the rodent to the start of its tail. The value "u" may also represent a size of the rodent measured perpendicular to the major axis of its torso, for example, a distance between the 2 front limbs. One of ordinary skill will recognize that the value "u" may be empirically determined so as to calculate a value that is small enough to provide useful data for accurately monitoring live subjects but is large enough to help minimize the length "P" of the coaxial piezoelectric cable 100.

Figure 7A:
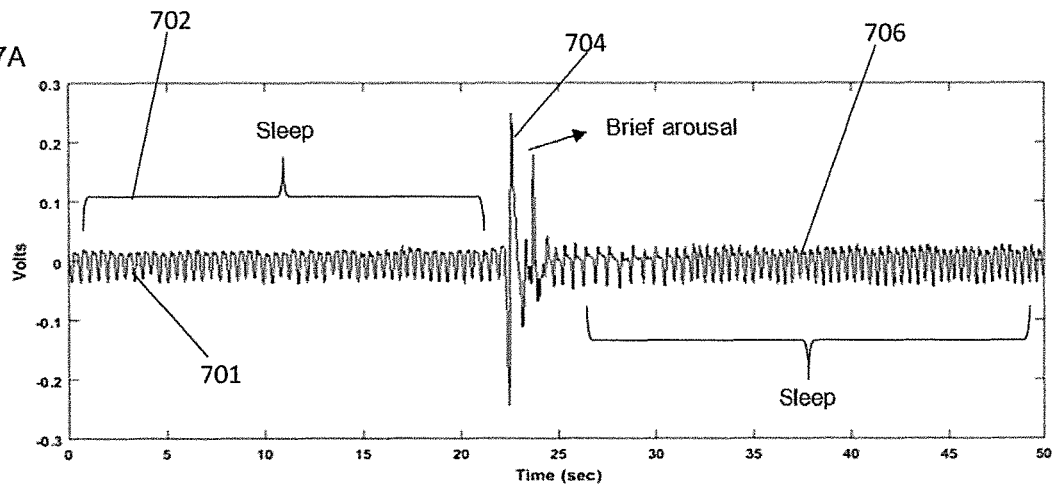
FIG. 7A depicts example piezoelectric data obtained from a rodent during a sleep state with a brief arousal in accordance with the principles of the present invention.

FIG. 7A depicts example piezoelectric data obtained from a rodent during sleep and wake states in accordance with the principles of the present invention. This piezoelectric data was plotted as line 701. The animal was asleep except for a brief arousal around second 22. The breathing rate, estimated as number of periods per unit time, was 2 Hz (breaths/sec). As depicted, section 702 depicts a first period of sleep, 704 depicts a brief arousal, and 706 depicts a second period of sleep in line 701.

Figure 7B:
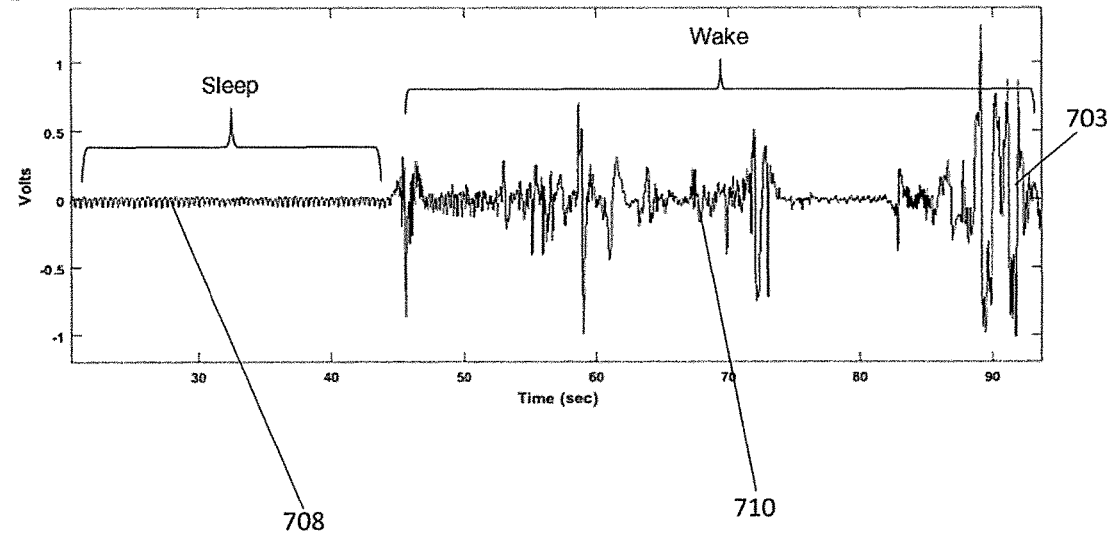
FIG. 7B depicts example piezoelectric data obtained from a rodent during sleep and wake states in accordance with the principles of the present invention.

FIG. 7B depicts example piezoelectric data obtained from a rodent as the rodent transitions from a sleep to an active wake state at second 45 in accordance with the principles of the present invention. This example data was plotted as line 703. As depicted, section 708 represents a period of sleep, and section 710 represents a period of wakefulness.

When placed in the vicinity of or in contact with an animal, the coaxial piezoelectric cable 100 may produce an electrical signal in response to the animal's movement to a different location within the cage, the animal's movement (e.g., shivering) while remaining in the same location, the displacement of air due to breathing (inhalation and exhalation), and the movement of the diaphragm and chest of the animal. For larger mammals, the piezoelectric sensor, placed appropriately, can also pick up the rate of contractions of the heart. FIGS. 7A and 7B show example of piezoelectric data obtained from a mouse under various physiological states. The data in these figures was collected using one piezoelectric cable 100, kept underneath a cage housing one animal. FIG. 7A shows a period when the mouse was sleeping but had a brief arousal at approximately the 22 seconds time point. The example piezoelectric signal of FIG. 7A is evidence of an oscillatory piezoelectric signal obtained during sleep which primarily comes from breathing (inhalation and exhalation) and chest and diaphragm movement. The breathing rate can be estimated by counting the number of periods occurring in a unit time. In FIG. 7A, the mouse was breathing at around 2 Hz (breaths/sec). FIG. 7B depicts a transition of the monitored animal from a state of sleep (seconds 1 to 45) to an active wake state (second 45 onwards). The signal amplitude shown in FIG. 7B is low during the first 45 seconds probably due to lack of arousal or other motor movement of the animal. The signal amplitude was higher after second 45 likely due to arousal, body movement, and/or motor movement of the animal.

The example data in FIGS. 7A-7E was collected using one piezoelectric cable 100, kept underneath a cage 204, 402a, 402b, 402c housing one rodent 202. Much of this data was collected during the rodent's sleep. The phenomenon of sleep is seen across mammals and other species like reptiles, birds, fish, and some invertebrates. The exact reason and mechanisms of sleep are still unknown but it's widely accepted that it plays an important role in recovery from illness or injury, as well as memory and cognitive performance. Sleep can be broadly classified into 2 stages (or phases), Rapid eye movement (REM) sleep and Non rapid eye movement (NREM) sleep. During NREM sleep, the body releases hormones essential for growth and development, grows and repairs tissues, and strengthens the immune system. REM sleep provides energy to body and activates the brain.

Figure 7C:
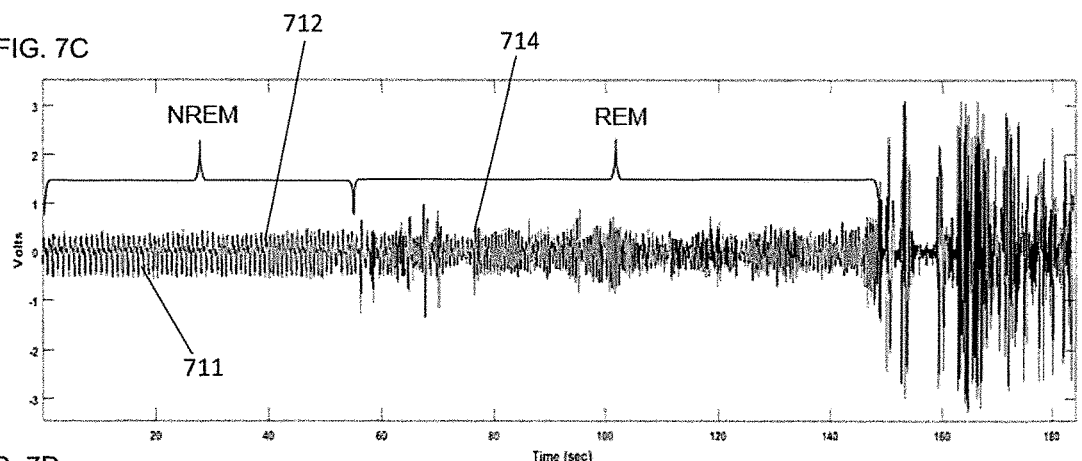
FIG. 7C depicts example piezoelectric data obtained from a rodent during REM sleep, NREM sleep, and wake states in accordance with the principles of the present invention.

FIG. 7C depicts an example of piezoelectric data obtained from a rodent during transition from NREM sleep (first 50 seconds) to REM sleep (seconds 50-150) to a wake state (after approximately second 145 to 150) in accordance with the principles of the present invention. This piezoelectric data is plotted as line 711. Section 712 depicts a period of Non-REM sleep, and section 714 depicts a period of REM sleep.

Figure 7D:
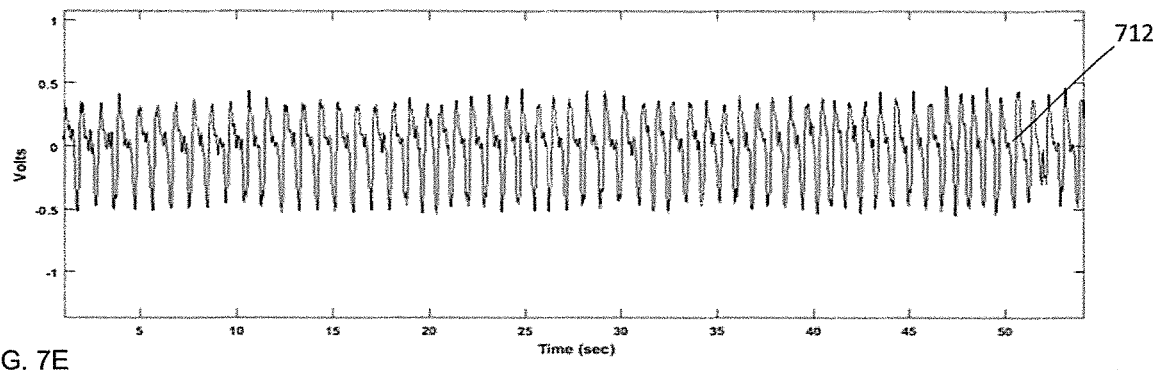
FIG. 7D depicts the NREM portion of the data of FIG. 7C in accordance with the principles of the present invention.

FIG. 7D shows the NREM section 712 of the data of FIG. 7C in accordance with the principles of the present invention. During NREM sleep, the data shows a regular, periodic breathing pattern.

Figure 7E:
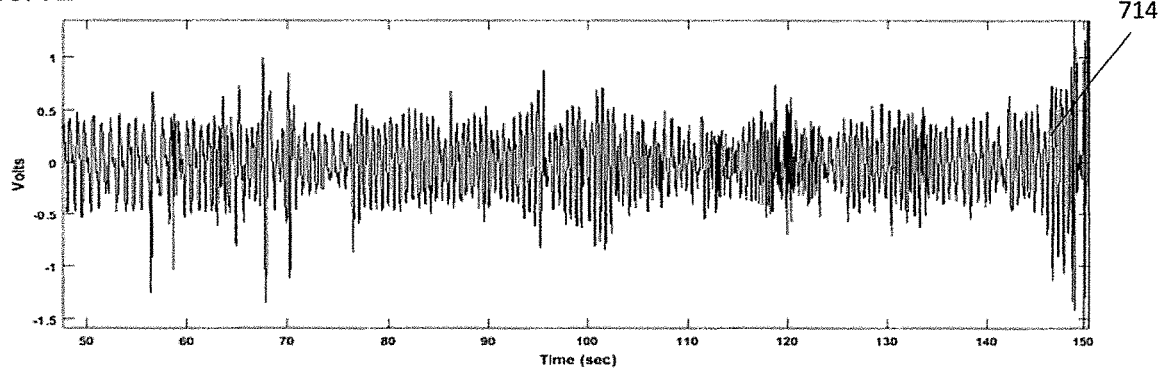
FIG. 7E depicts the REM portion of the data of FIG. 7C in accordance with the principles of the present invention.

FIG. 7E depicts the REM section 714 of data of FIG. 7C in accordance with the principles of the present invention. During REM sleep, the data shows slightly irregular and aperiodic breathing. In addition, the signal amplitude during REM sleep tends to be lower than that caused by bodily movement during the wake state which follows.

Figure 8:
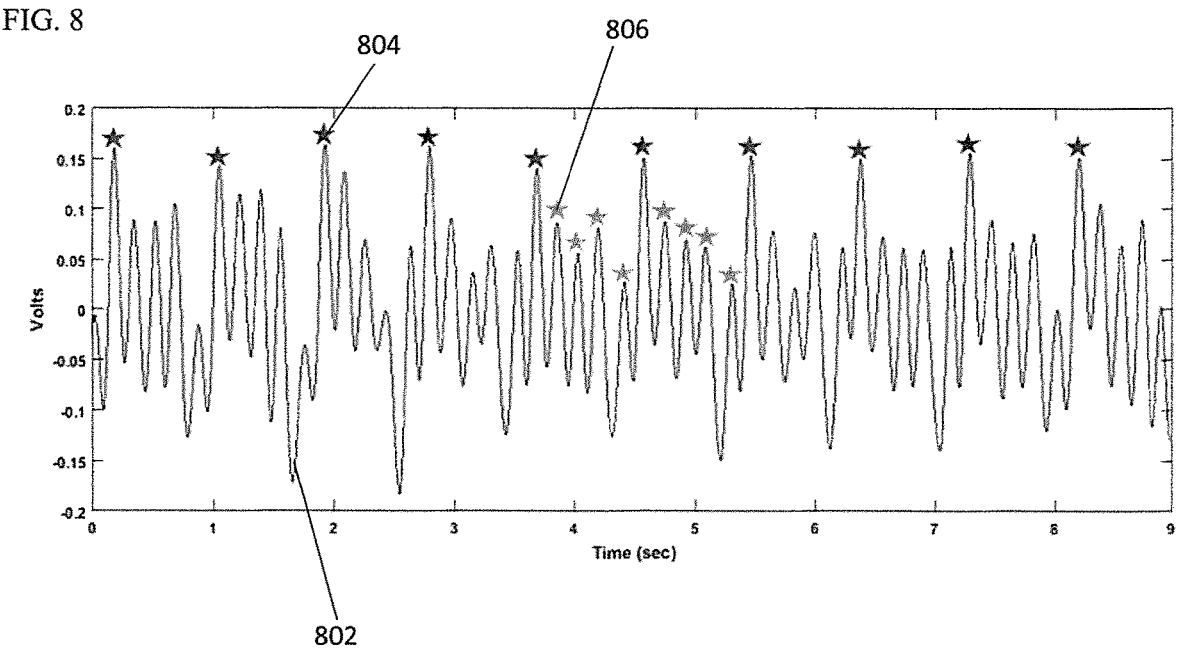
FIG. 8 depicts example data exemplifying both heartbeat and breathing in accordance with the principles of the present invention.

FIG. 8 depicts piezoelectric data exemplifying both heartbeat and breathing in accordance with the principles of the present invention. This data is plotted as line 802. This data was obtained from a rodent during a period of sleep. As explained previously, breathing may cause pressure on the coaxial piezoelectric cable 100 through movement of the chest of the monitored animal. For larger mammals, the coaxial piezoelectric cable 100 can pick up the rate of contractions of the heart in addition to breathing. The peaks marked by dark stars 804 represent the end of inhalation and the peaks marked by light stars 806 represent the end of systole (e.g. the end of the phase of heart muscle contraction sending blood into the arteries). The inverse of the time interval between two dark stars 804 indicates the breathing rate. The inverse of the time interval between two light stars 806 indicates the heart rate.

Figure 9A:
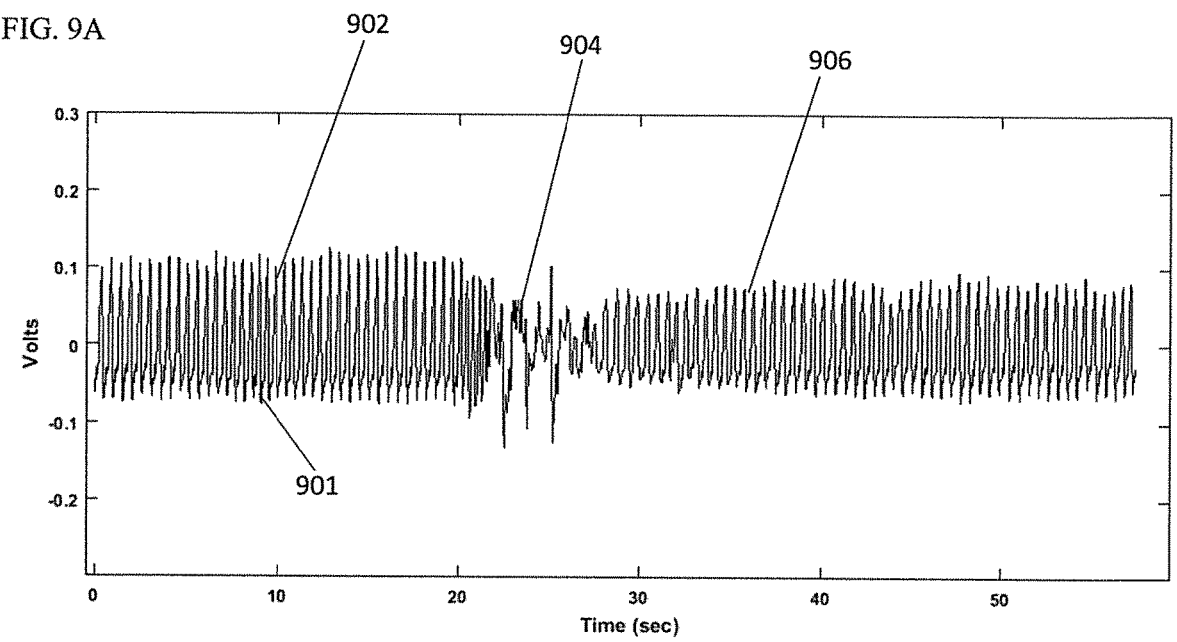
FIG. 9A depicts example data corresponding to a time period in which a rodent was sleeping with a brief arousal between seconds 20 and 30 in accordance with the principles of the present invention.
Figure 9B:
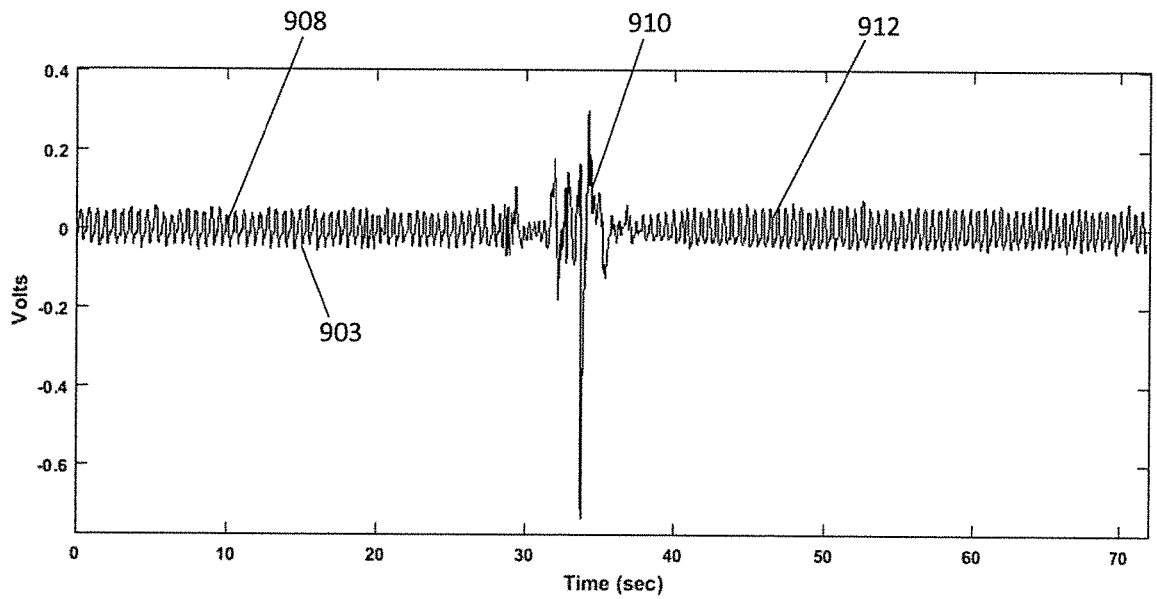
FIG. 9B depicts example data from the coaxial piezoelectric cable in accordance with the principles of the present invention.
Figure 9C:
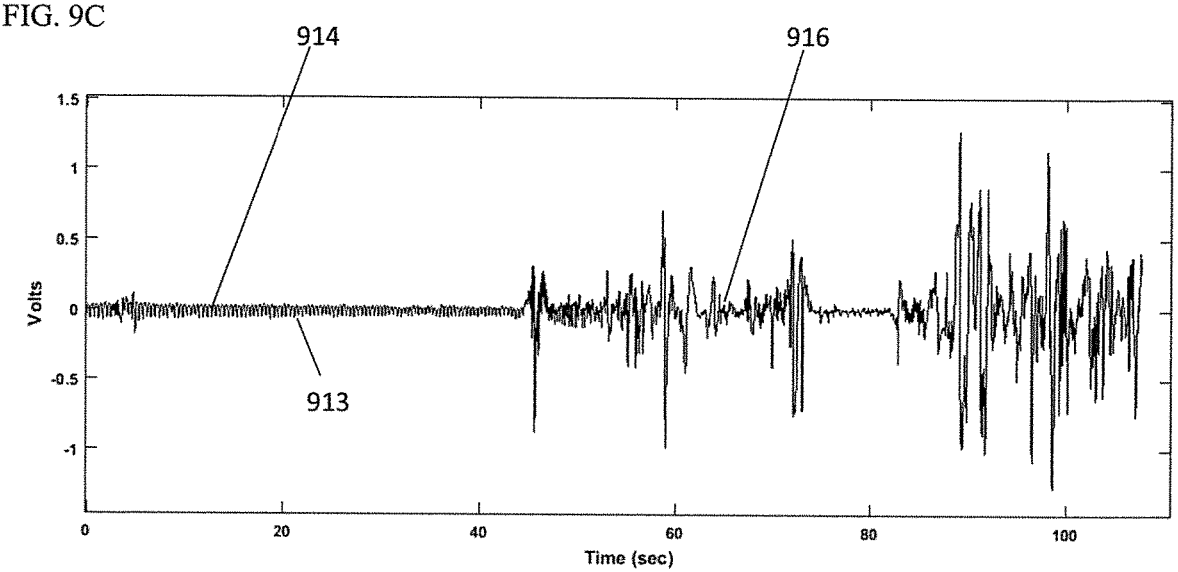
FIG. 9C depicts example data from the coaxial piezoelectric cable corresponding to a transition from sleep during the first 40 seconds to active wake in accordance with the principles of the present invention.

FIGS. 9A-9C show examples of a signal obtained via the coaxial piezoelectric cable 100 with a mouse in the cage 204, 402a, 402b, 402c. This data was plotted as line 901. The signal of FIG. 9A is representative of example piezoelectric data corresponding to a time period in which the mouse was sleeping (denoted as section 902) with a brief arousal between seconds 20 and 30 (depicted as section 904) in accordance with the principles of the present invention. Section 906 depicts a second section of sleep. During sleep, the live subject may have a slower and regular breathing rhythm (inhalation and exhalation), which manifests as periodic variations in the piezoelectric data and, thus, produces a periodic, or oscillatory, signal. The period of this signal during sleep allows for derivation of a respiration rate, or breathing frequency (breaths/second) of the monitored animal. The amplitude of the brief arousal relative to the amplitude during sleep gives information about the nature of the arousal. For example, the difference in the arousal amplitudes between FIGS. 9A and 9B suggests that the animal could have changed the position of its head without moving the whole body in FIG. 9A while the amplitude of FIG. 9B suggests movement of a substantial portion of the animal's body.

FIG. 9B depicts example data from the coaxial piezoelectric cable 100 in accordance with the principles of the present invention. This data was plotted as line 903. Sections 908 and 912 depict respective periods of sleep. Section 910 depicts a period of brief arousal with motor movement. As noted above, the larger scale of the data amplitude compared to FIG. 9A suggests a change in body position of the animal, rather than a non-motor movement of the head or limb.

FIG. 9C depicts example data from the coaxial piezoelectric cable 100 corresponding to a transition from sleep during the first 40 seconds to active wake in accordance with the principles of the present invention. This data is plotted as line 913. In the first 40 seconds (section 914), the animal was stationary and the only variations in pressure were coming from the inhalation and exhalation of air due to breathing and the corresponding movements of the diaphragm and ribcage. The amplitude of the periodic signal during breathing may depend on how much surface area of the body is in contact with the coaxial piezoelectric cable 100 or the film 210b of the piezoelectric coil assembly. Forty seconds onward (section 916), when the animal is awake and active, amplitudes of the signal rise likely due to a constant change in position or location of the animal (larger mass movement) in addition to the faster breathing rates and higher tidal volumes during inhalation and exhalation.

Figure 9D:
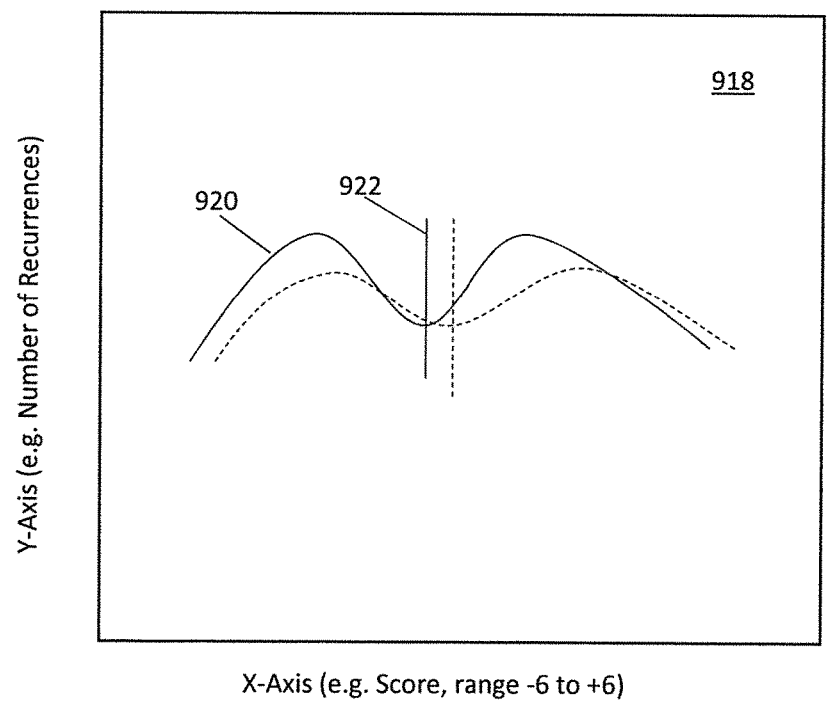
FIG. 9D depicts a curve that is useful in the analysis of signals for determining how to classify the rodent in one or more different states in accordance with the principles of the present invention.

As described in detail below, features of the piezoelectric sensor data (e.g., the signal 701 of FIG. 7A) can be combined together, such as by linear discriminant analysis (LDA) to generate a respective score or value for each of a plurality of sample periods that allow classifying the rodent into belonging to one of a plurality of different states. The LDA generated score or value will henceforth be referred to as the decision statistic (DS). FIG. 9D depicts a curve 918 joining the centers of bins of a histogram of such values and is useful in the analysis of the signal to determine how to classify the rodent in one or more different states in accordance with the principles of the present invention. For example, the histogram 918 may be plotted to determine a binary threshold for comparative determination of a classification, such as wake or sleep. In embodiments wherein a binary classification is being determined, the histogram 918 may be a bimodal distribution 920, where each cluster represents a class into which the data gets divided using the threshold 922 (for example Sleep and Wake cluster). Example signal features that can be used in combination to calculate each value of the DS for the bimodal distribution 920 can include features such as signal envelope, peak frequency, frequency, power, amplitude, skewness, etc.

As an initial step, data may be collected and observations may be made for a particular type of rodent (e.g. mice, rats, etc.) to determine the combination of signal features to use when classifying rodent states and the corresponding weight for each of those signal features. For example, the corresponding weights may be selected to correspond with the effect of each signal feature on correctly classifying the rodent into one of a plurality of classifications (e.g. wake/sleep, REM/non-REM, etc.). The weights may be selected based on data corresponding to a large number of rodents of a particular type.

Once the signal features and their respective weights are determined, that same weighted linear sum formula can be used for real-time classification of a rodent based on features of the signal (i.e., the received data) from the coaxial piezoelectric cable 100. The weighted linear sum values form the decision statistic (DS). As part of this real-time classification analysis one or more respective threshold values can be calculated for each rodent that are indicative of the different classifications in which the rodent could be classified. For example, if the rodent is being classified into one of two states, then a single threshold value can be calculated such that the values of the DS below the threshold indicate the rodent is in a first state and DS values above the threshold indicate the rodent is in a second state. As another example, determining two different threshold values for each rodent would allow classifying that rodent into one of three possible states.

Accordingly, the first step of determining the threshold may comprise determining a DS (i.e. signal score) based on a sum of terms wherein each term is a product of the corresponding weights and features of the signal at a given interval (e.g., every 2 seconds). Then, the total number of times each score occurred over a predetermined period is calculated (e.g. 24 hours may be the predetermined period when classifying sleep/wake state). A corresponding histogram may be plotted for each predetermined period. The score (e.g. −6 to +6 for sleep/wake) may be represented on the X axis, whereas the number of recurrences of each score may be represented on the Y axis. Several corresponding histograms may be plotted for several corresponding periods, such as seven histograms representing seven days.

The corresponding histograms (e.g., 920 of FIG. 9D) may apply to a particular rodent to be studied in real time (in a later step). The different histograms for a rodent may each have an inflection point that may vary from each other in value along the x-axis. This variation may account for environmental and/or peculiar aspects of the particular rodent. The different inflection point values along the x-axis may be statistically combined, such as for example by being averaged together or by using a median value from a set of values, to calculate a threshold for the rodent.

The threshold may be used in real time classifying of the rodent into one of a plurality of possible states or it can be applied to the data post-collection. For example, the threshold may be used when analyzing the detected signal from the coaxial piezoelectric cable. The DS (e.g. weighted linear sum) obtained from the detected signal features may be compared to the threshold. When the DS values are below the threshold, the rodent may be classified as being awake, because the detected activity level may correspond with a waking rodent. When the DS values are above the threshold, the rodent may be classified as being asleep, because the detected activity level may correspond with a sleeping rodent.

Figure 10A:
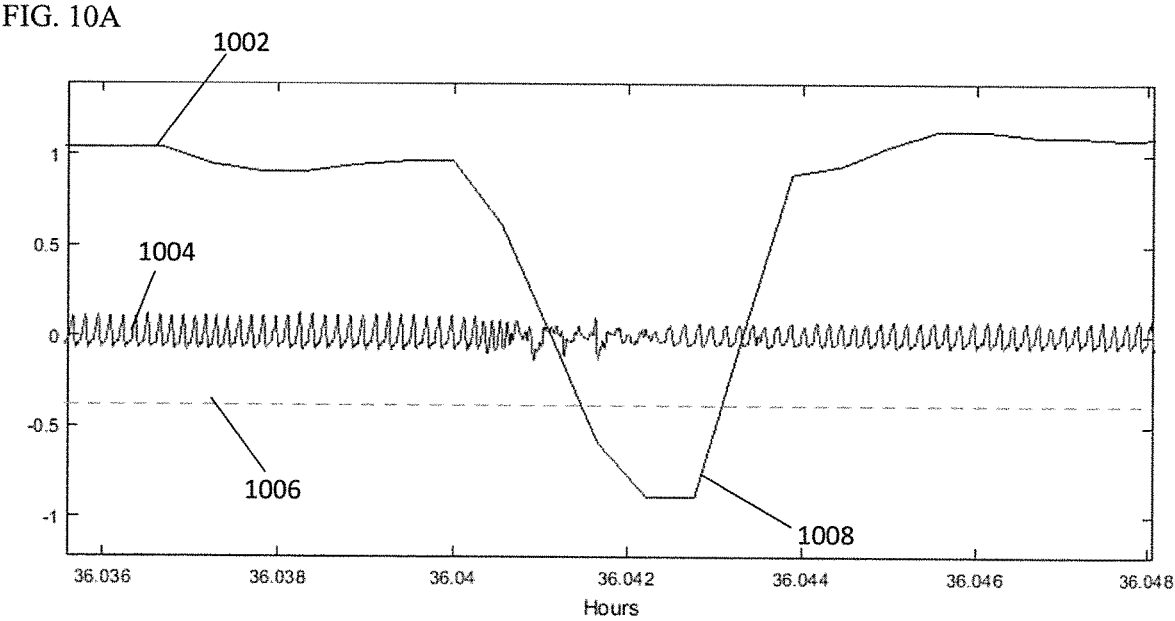
FIG. 10A depicts an example application of a statistical method to the piezoelectric data of FIG. 9A to classify the data in to "sleep" or "wake" states in accordance with the principles of the present invention.

As mentioned, the X axis may plot a DS calculated based on signal features, such as signal envelope, peak frequency, frequency, power, amplitude, skewness, etc. In one example embodiment of the threshold determination process described above, corresponding to a sleep/wake determination, the DS may be between −6 and +6. A DS value between −6 (inclusive) and zero may indicate that the rodent is awake. A DS value of −6 will indicate that the rodent is definitely awake. Similarly, a DS value between zero and +6 may indicate that the rodent is asleep with a value of +6 indicating that the rodent is definitely asleep. In this example, the value "0" is assumed to be the threshold used to classify the rodent into one of two states for a particular sampled interval. However, as mentioned above, that threshold value can be adjusted based on previously collected data for a particular rodent FIG. 10A depicts an example application of a statistical method to the piezoelectric data and signal of FIG. 9A to classify the data in to "sleep" or "wake" states in accordance with the principles of the present invention. One example statistical method (e.g., LDA, as described above) can use a decision statistic (DS) 1002 comprising of a weighted linear sum of the set of features that were extracted periodically from the piezoelectric data 1004 and then compare the DS values 1002 against a threshold 1006 to classify the data. Example signal features useful for classification of rodent activity include the signal envelope, peak frequency, power, skewness, probabilistic/spectral, etc. The horizontal dotted line represents the threshold 1006 as determined by the classifier based on the signal features. The solid line 1002 overlaying the data represents the DS (weighted linear sum) 1002 of the features. The data 1004 is classified as "sleep" when the value of DS 1002 is above the threshold 1006 and "wake" when the DS 1002 is below the threshold 1006.

Figure 10B:
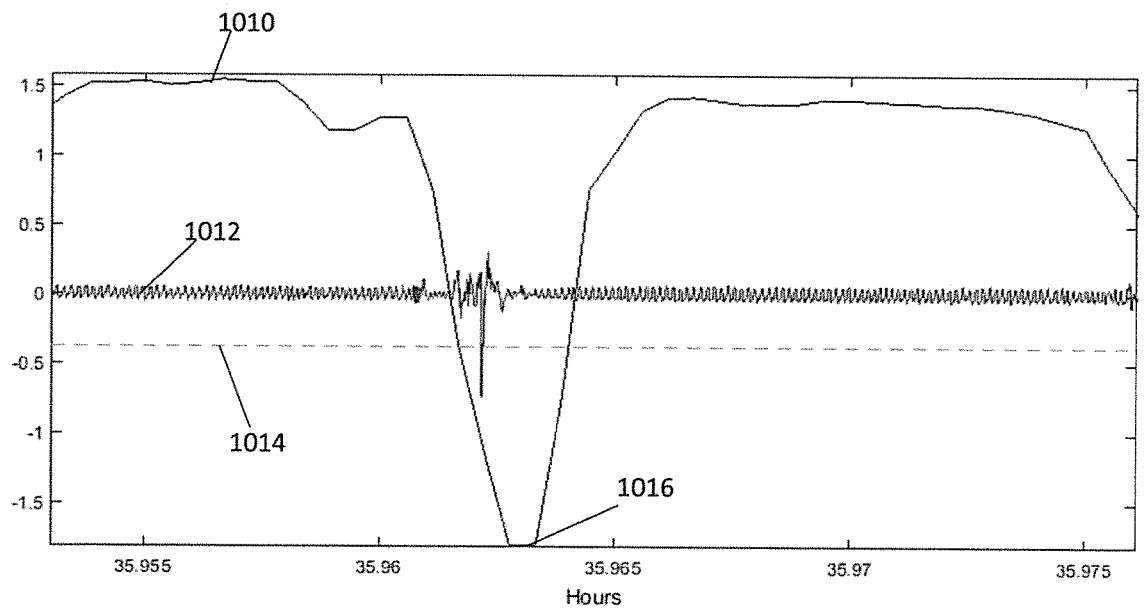
FIG. 10B depicts a further example application of a statistical method to the piezoelectric data of FIG. 10B to classify the data into "sleep" or "wake" states in accordance with the principles of the present invention.

FIG. 10B depicts a further example application of a statistical method to the piezoelectric data of FIG. 10B to classify the piezoelectric data 1012 into "sleep" or "wake" states in accordance with the principles of the present invention. FIGS. 10A and 10B show the DS' (weighted linear sum) 1002 and 1010 respectively, dropping below the threshold (1006 and 1014, respectively) during the brief arousal periods (1008 and 1016, respectively). The DS 1002, 1010 returns above the threshold 1006, 1014 in post-arousal sleep.

Figure 10C:
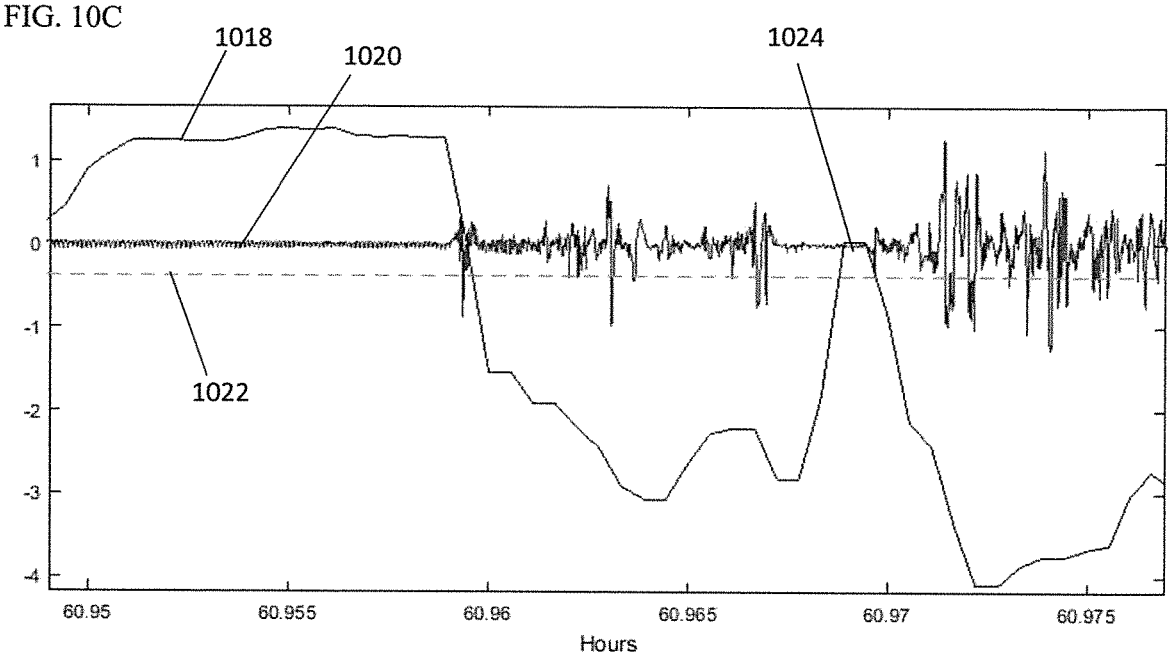
FIG. 10C depicts a further example application of a statistical method of the piezoelectric data of FIG. 10C to classify the data into "sleep" or "wake" states in accordance with the principles of the present invention.

FIG. 10C depicts a further example application of a statistical method to the piezoelectric data 1020 of FIG. 10C to classify the piezoelectric data 1020 into "sleep" or "wake" states in accordance with the principles of the present invention. Once the animal is awake, the DS 1018 stays below the threshold 1018 unless the animal tries to go back to sleep or is very stationary as depicted at point 1024.

Figure 11:
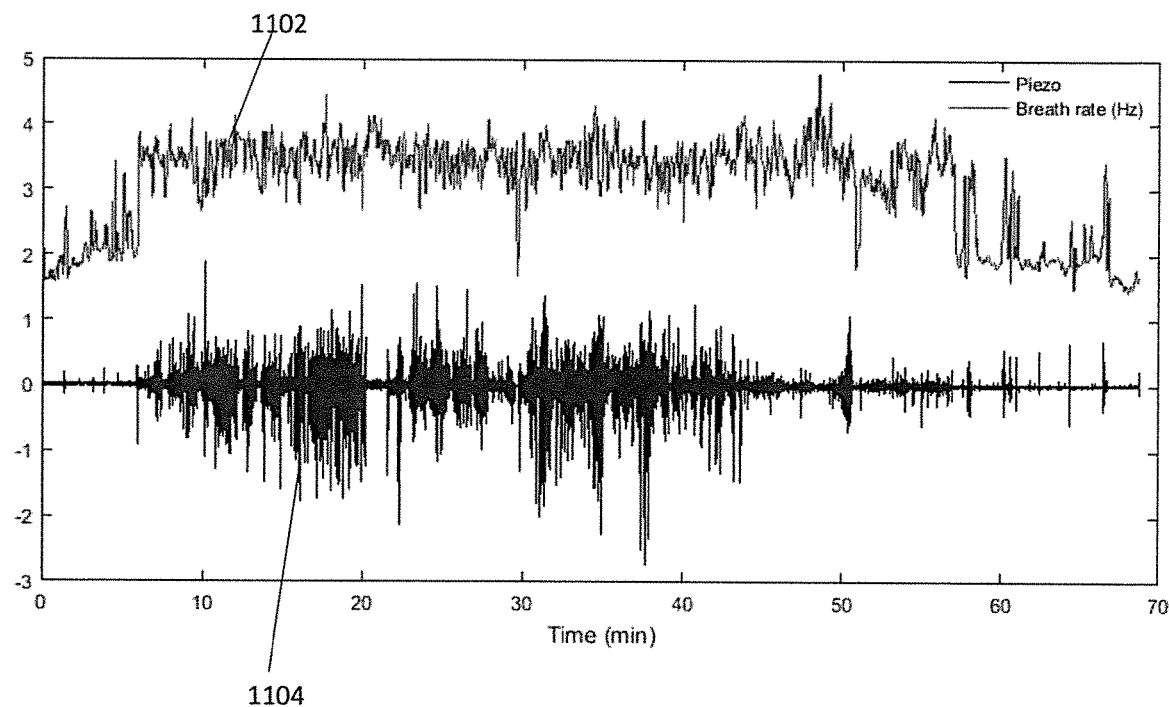
FIG. 11 depicts example data related to a respiration rate of a rodent in accordance with the principles of the present invention.

Classification of the piezoelectric data is not limited to gross "sleep" and "wake" states, but may be sensitive enough for finer distinctions within each state. Sleep can be further classified into rapid eye movement (REM) sleep or Non-rapid eye movement (NREM) sleep. Similarly, wake can be further classified into inactive wake or active wake. Use of sophisticated statistical methods allow for finer distinctions using the piezoelectric data. For finer distinctions, statistical predictive models such as Random forests, Classification and Regression trees (CART), Support vector machines, decision trees, neural networks, etc. can be used to determine the probability of assigning a given set of data to a particular class. FIG. 11 depicts an example of the piezoelectric data collected while tracking the respiration rate of the rodent in accordance with the principles of the present invention. The top line 1102 indicates the respiration frequency (breath rate in breaths/second). The bottom line 1104 indicates a signal representative of the detected piezoelectric data. The respiration rate may increase in response to an increase in animal activity. Furthermore, the respiration rate may decrease in response to a decrease in animal activity. The example signal of FIG. 11 shows how the piezoelectric data can be used to track respiration rates. This data was collected from a 70 minute span. The respiration rates were estimated using a peak analysis. The means of the inter-peak intervals, obtained from 8 second data windows, were used to estimate the respiration rates. The respiration rates were estimated every two seconds.

Figure 12:
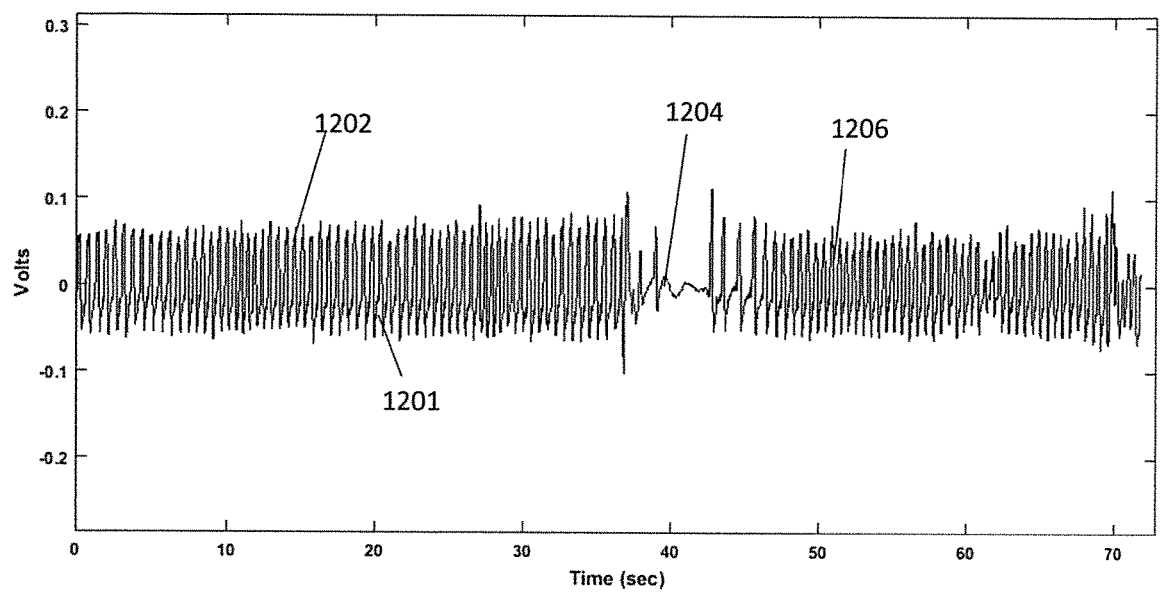
FIG. 12 depicts data indicating sleep apnea using a monitoring system in accordance with the principles of the present invention.

FIG. 12 depicts the detection of sleep apnea using the monitoring system in accordance with the principles of the present invention. Sleep apnea is a common sleep disorder characterized by a brief cessation or very shallow breathing during sleep. It can occur due to obstruction or collapsing of the airway (obstructive apnea) or due to lack of brain signaling to the airway muscles responsible for breathing (central apnea). A pause in breathing lasting longer than the duration of two breath cycles during sleep is considered an episode of apnea. The mean duration of the breath cycle in the above data was 0.55 seconds and the pause in breathing lasted for about 3 seconds between seconds 39 and 42. In the piezoelectric data plotted as line 1201, a brief period of sleep apnea can be seen at point 1204. Intervals 1202 and 1206 represent sleep that is uninterrupted by apnea.

Figure 13A:
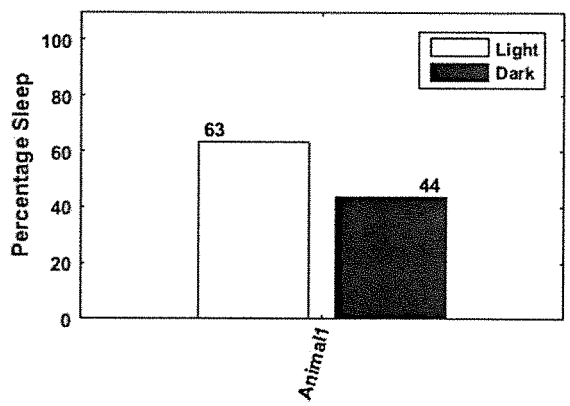
FIGS. 13A and 13B depict sleep-related data collected using a monitoring system in accordance with the principles of the present invention.
Figure 13B:
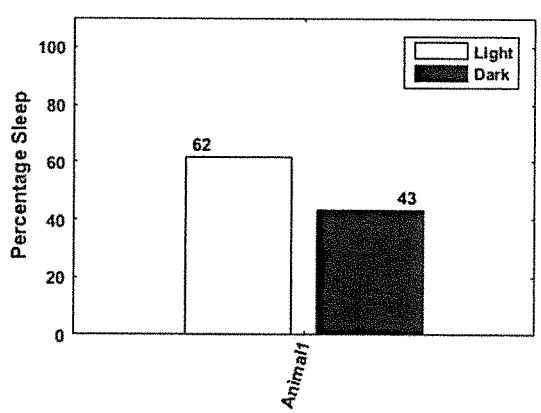

FIGS. 13A-13B compare the performance of the coaxial piezoelectric cable 100 with a piezoelectric sheet (7"×7") in tracking animal sleep and activity. In separate trials, data was collected using a coaxial piezoelectric cable and then a piezoelectric sheet, with the same animal (a mouse). Each recording was 2 days long. The animal was exposed to natural light and dark cycles. In both trials, the different types of sensors were placed between the cage floor and film 210b. The light and dark periods were assumed to be 12 hours each.

FIG. 13A depicts data from a first trial representative of the distribution of sleep between the light and dark periods using the coaxial piezoelectric cable in accordance with the principles of the present invention.

FIG. 13B depicts data from a second trial representative of the distribution of sleep between the light and dark periods using the piezoelectric sheet.

Figure 14:
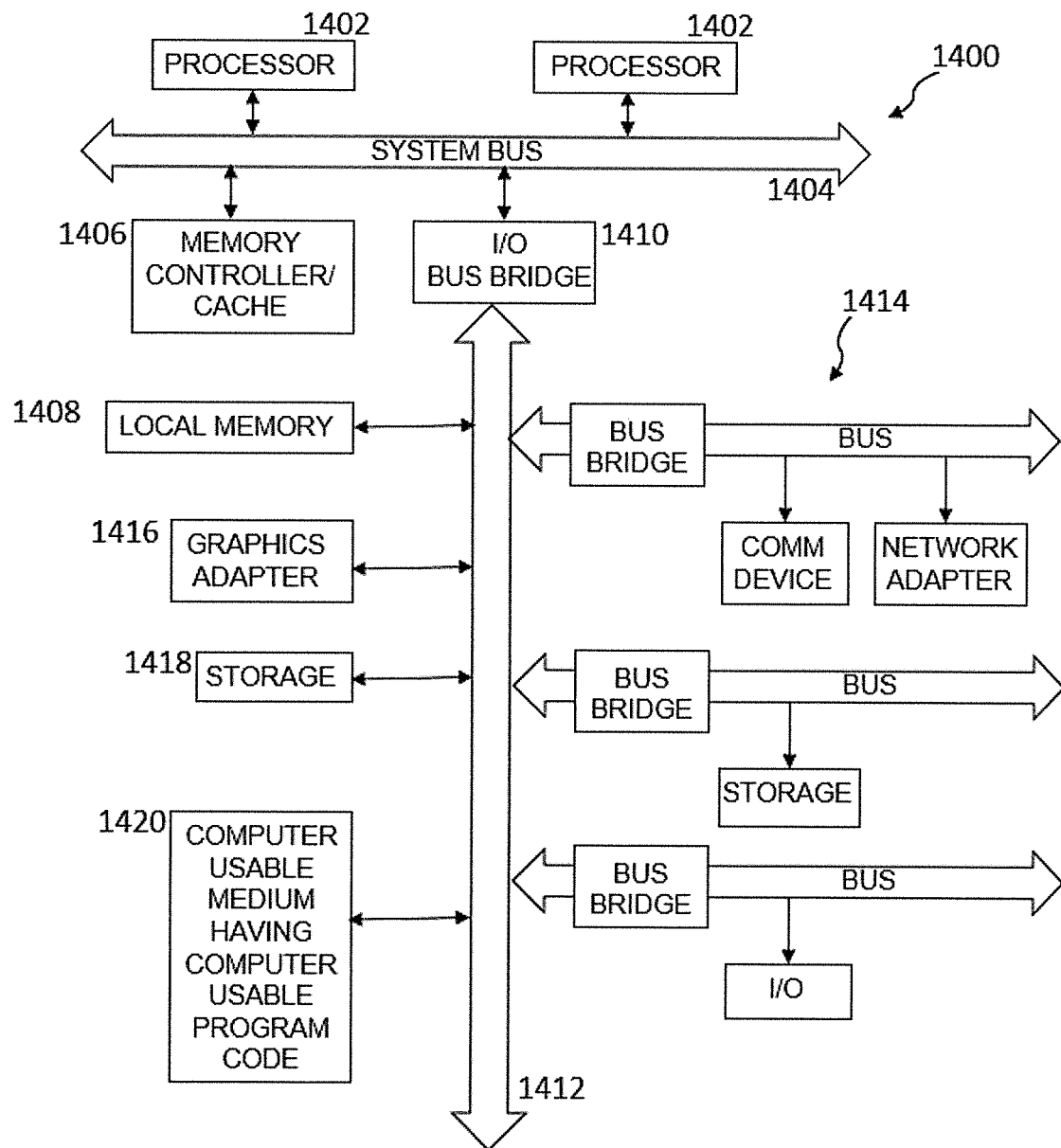
FIG. 14 depicts an example block-level hardware diagram of the data analyzer of FIG. 2 in accordance with the principles of the present invention.

FIG. 14 depicts a block-level diagram of a data analyzer 1400 that is the same as or to the data analyzer computer system 216 of FIG. 2 in accordance with the principles of the present invention. The data analyzer 1400 may provide a platform that allows execution of animal monitoring software that can also include data collection software. Such software could be the only software executing on the data analyzer 1400. Alternatively, the data analyzer computer system 216 could include an operating system, such as Microsoft Windows, Linux, iOS, Android, etc., and the animal monitoring and data collection software would be compatible with the operating system. The piezoelectric signals may be received continuously, at a predetermined interval(s), based on movement, or other variables of research interest.

Alternatively, the data analyzer 1400 could receive voltage information and could approximate the level of movement as described above based on the size and distance of the animal. Furthermore, the data analyzer 1400 can execute smoothing algorithms for averaging areas or creating a weighted linear sum. For example, maps or charts depicting the detected voltage from the coaxial piezoelectric cable and/or calculated lines, such as the weighted linear sum, may be displayed to the user via a screen. The data may also be stored as an array correlating multiple respective animal's detected voltages at a given time. This data could then be analyzed to show movement, changes in head positioning, other behavior patterns, or physiological states. The data analyzer 1400 could then be used to correlate this data with other experimental factors to form relationships between the experimental variables. Correlations in piezoelectric data may be used to classify the rodent's movement into a physiological state. In this manner, fine movement and activity of an animal may be detected and associated with behaviors such as grooming, random eye movement (REM) sleep, non-REM sleep, eating, hyperactivity or other behaviors. The data analyzer 1400 could also be used for automatic classification of these behaviors based on patterns observed in the piezoelectric data. For example, presence near the food as well as head movements consistent with eating may give piezoelectric data that can be correlated to identify an eating behavior. The eating behavior could then be detected directly through analysis of the piezoelectric data rather than requiring video or direct observation. One example of a useful software in these analyses is MATLAB. By using the data analyzer 1400 to provide analysis and automation during experiments, animal behavior experiments may be scaled for use with multiple monitored live subjects.

The data analyzer 1400 may be any electronic device capable of electronic signal manipulation. Storage by the data analyzer 1400 may utilize a hard drive, memory, or other storage device. Receiving a selection, receiving a user selection, receiving a selected element, and other interactions with the user may be accomplished by event detection, drag and drop operations, queries, interrupts, signals, polling, dialog, command, etc. Selections or user selections may be useful in setting parameters for experiment automation, such as to capture data points at a specified interval wherein the selection may comprise a time interval. Other selections may be made, such as to capture a data point and record time based on a detected behavior pattern.

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor 1402 of the data analyzer 1400, a general purpose computer, special purpose computer, or other programmable data processing apparatus to produce a machine, such that the instructions, which execute via the processor 1402 of the data analyzer 1400 or other programmable data processing apparatus, create means for implementing the functions/acts specified in the flowchart and/or block diagram block or blocks.

These computer program instructions may also be stored in a computer readable medium 1420 that can direct the data analyzer 1400, other programmable data processing apparatus, or other devices to function in a particular manner, such that the instructions stored in the computer readable medium 1420 produce an article of manufacture including instructions which implement the function/act specified in the flowchart and/or block diagram block or blocks.

The computer program instructions may also be loaded onto the data analyzer 1400, a computer, a microcontroller, other programmable data processing apparatus, or other devices to cause a series of operational steps to be performed by the data analyzer 1400, other programmable apparatus or other devices to produce a data analyzer 1400 implemented process such that the instructions which execute on the data analyzer 1400 or other programmable apparatus provide processes for implementing the functions/acts specified in the flowchart and/or block diagram block or blocks.

The data analyzer 1400 may comprise a symmetric multiprocessor (SMP) system or other configuration including a plurality of processors 1402 connected to system bus 1414. Alternatively, a single processor 1402 may be employed. Also connected to system bus 1414 is memory controller/cache 1406, which provides an interface to local memory 1408. An I/O bridge 1410 is connected to the system bus 1404 and provides an interface to an I/O bus 1410. The I/O bus 1410 may be utilized to support one or more buses and corresponding devices, such as bus bridges, input output devices (I/O devices), storage, network adapters, etc. Thus, a network adapter may be coupled to the system to enable the data processing system to become coupled to other data processing systems or remote printers or storage devices through intervening private or public networks.

Also connected to the I/O bus 1410 may be devices such as a graphics adapter 1416, storage 1418 and a computer usable storage medium 1420 having computer usable program code embodied thereon. The computer usable program code may be executed, e.g., by the processor(s) to implement any aspect of the present invention, for example, to implement any aspect of any of the methods, processes and/or system components illustrated in any of the figures of the present application. Moreover, the computer usable program code may be implemented in the local memory 1408 or other suitable storage medium. The storage 1418 may store resources useful in implementing the features previously described. For instance, the storage 1418 can store the computer instructions which, when executed, implement any of the methods or actions disclosed herein.

The data analyzer 1400 may be configured for acquiring sensor signals in accordance with the principles of the present invention. The data analyzer 1400 may be capable of receiving the piezoelectric data over an input interface and sending the piezoelectric data over an output interface. The data analyzer 1400 may also perform operations on and modify the piezoelectric data such as creation of an array to associate the piezoelectric data with the corresponding source coaxial piezoelectric cable 100.

The data analyzer 1400 may comprise a processing unit (CPU) 1402, local memory 1408, peripherals and interfaces, and a general purpose input/output (I/O) interface. The data analyzer 1400 may further comprise local storage 1418. The local storage 1418 may be used to store variables for complex calculations. The local memory 1408 may interface with the CPU 1402 via a memory interface. The memory interface may allow storage of calculated values, variables, constants, or any other important electronic signals onto the physical local memory 1408. The memory interface may include one or more direct memory access controllers. Of course, part or all of the local memory 1408 may be committed to the computer usable storage medium 1420, in which data relevant to the operation of the program is stored. The computer usable storage medium 1420 may also be organized into useful data structures such as a stack or heap. The peripherals and interface and the general purpose I/O interface may interface to external input or output devices. Examples of external input or output devices include any electronic device capable of sending or receiving an electronic signal such as keyboards, mice, printers, scanners, digital sensor, analog sensors, Ethernet, analog to digital converters, ADC, UART, USB etc. The computer usable storage medium 1420, local memory 1408, peripherals and interface, and general purpose I/O interface may be contained on the circuit board of the CPU 1402. In other embodiments, any of these parts may be external to the CPU 1402.

Figure 15:
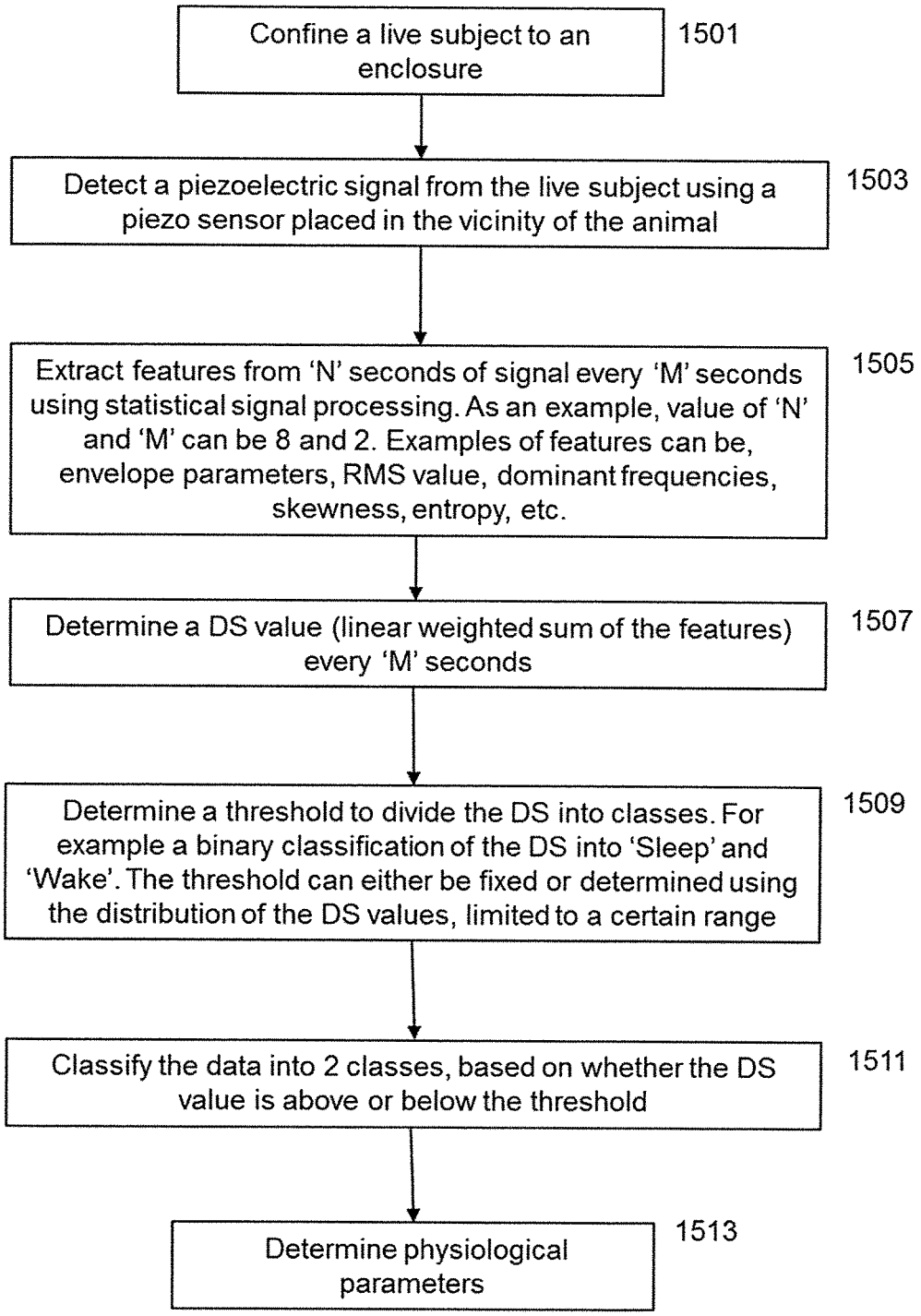
FIG. 15 depicts a flowchart of an example method of classifying a monitored live subject in accordance with the principles of the present invention.

FIG. 15 depicts a block-level diagram of a method of classifying a monitored live subject in accordance with the principles of the present invention. For example, the classification may be binary, such as "alive/dead," "sick/well," "sleep/wake," "active/inactive," "REM/NREM," or any other identifiable binary classification of movement of the live subject. Additionally, the classification may apply to a specific moment in time (e.g. sleep/wake, and other classifications, may change second by second). More generally, the present system provides for sensing one or more physiological states and parameters of one or more monitored live subjects. These physiological states and/or parameters include activity level (e.g., movement in bodily position, movement of location within the cage, the rate of movement within the cage, lack of movement, grooming, eating, drinking, shivering, etc.); the phase of sleep (e.g., deep sleep, light sleep, REM, NREM, etc.); respiratory effort (e.g., breathing rate); and measurements related to heart rate.

In step 1501, the live subject may be confined to an enclosure. The live subject may be a rodent, a human, or any other animal capable of being used as a model for human bodily function, disorder, disease, etc. The enclosure may be a cage 204, 402*a*, 402*b*, 402*c* as disclosed herein. Other enclosures may include tethers, a wireless pet fence system, or any other means of confining the live subject to the observation area.

Step 1503 can include detecting a piezoelectric signal from the live subject using the coaxial piezoelectric cable 100. The coaxial piezoelectric cable 100 may be placed near the cage 204, 402*a*, 402*b*, 402*c*, wherein "near" means placed such that movement of the live subject causes a detectable pressure change, or mechanical effect, on the coaxial piezoelectric cable 100. Example arrangements are disclosed above. Movements by the live subject may result in a piezoelectric electric signal from the piezoelectric cable 100 that may be detected.

In step 1505, several features from the piezoelectric signal may be extracted using statistical signal processing techniques. The features may be extracted from 'N' second long data segments every 'M' seconds. As an example, the values of 'N' and 'M' can be 8 and 2 respectively. Examples of features extracted can be envelope parameters, RMS value, dominant frequencies, skewness, entropy, etc.

In step 1507, a DS may be determined as weighted linear sum of features (e.g. parameters) extracted from the piezoelectric signal. One of ordinary skill will recognize that other statistical measures and techniques may be used without departing from the scope of the present invention. The weighted linear sum may then be plotted on the voltage versus time graph for visualization.

In step 1509, a threshold corresponding to a binary data classification may be determined. The binary data classification may comprise any binary identifier related to bodily movement, or other physiological parameter of the live subject. The threshold may be determined empirically by observation of data during both states of the binary data classification. Then, the threshold may be set to coincide with the transition between the two corresponding binary states. For example, piezoelectric data may be observed during the rodent's wake and sleep states. The threshold may then be set to coincide with the observed arousal of the rodent and/or the falling asleep of the rodent. As a further example, the rodent may be observed at a resting wake state and an active wake state. The threshold may be placed at the transition between activity and inactivity and/or the transition between inactivity and activity.

In some embodiments, the threshold may be determined using statistical techniques. For example, the threshold may be set by minimizing a weighted standard deviation of proposed thresholds within a range relative to the measured thresholds within.

In step 1511, the binary data classification may be determined based on whether the DS (weighted linear sum, or other statistically calculated value based on the piezoelectric data) is above or below a particular threshold value. The DS at a given time may be either above or below the threshold. When the DS is above a threshold, one counterpart of the binary classification may apply. Alternatively, when the DS is below the threshold, the alternate counterpart of the binary classification may apply. As described above with respect to FIGS. 10A and 10B, the system 200 of the present invention determines that the live subject is awake when the DS value is below the corresponding threshold. The system 200 further determines that the live subject is asleep when the weighted linear sum is above the threshold.

In addition to the binary classification just described with respect to step 1511, embodiments of the present system may also determine physiological parameters associated with the live subject, in step 1513. As described above with respect to FIG. 8, parameters related to the heart and respiration of the live subject can be detected.

Embodiments of the present invention include a cage for a mammal, comprising a plurality of generally planar surfaces, comprising a plurality of vertical surfaces, and a horizontal surface; and a coaxial piezoelectric cable at least indirectly coupled to one of the plurality of generally planar surfaces. Further embodiments include the cage, wherein the coaxial piezoelectric cable is in physical contact with at least a portion of the cage. Further embodiments include the cage, wherein the coaxial piezoelectric cable is encapsulated in a protective assembly, the protective assembly detachably positioned in physical contact with the cage. Further embodiments include the cage, wherein the protective assembly comprises a top layer having a first surface area substantially the same as a surface area of the horizontal surface, and a bottom layer having a second surface area substantially the same as the surface area of the horizontal surface, wherein the coaxial piezoelectric cable is positioned between the top layer and the bottom layer, the top layer provides a floor for the cage, and the bottom layer is located above the horizontal surface. Further embodiments include the cage, wherein the layout of the coaxial piezoelectric cable is arranged in a coil comprising a plurality of segments. Further embodiments include the cage, wherein a layout of the coaxial piezoelectric cable is arranged to provide uniform sensing coverage of the floor. Further embodiments include the cage, wherein the layout of the coaxial piezoelectric cable is arranged in a coil comprising a plurality of segments. Further embodiments include the cage, wherein a distance from any portion of one segment to a closest different segment is based on a size of the mammal. Further embodiments include the cage, wherein the distance is less than or equal to an average size, U, of the mammal. Further embodiments include the cage, wherein the plurality of vertical surfaces are arranged to form a rectangle comprising a width a and a length b, the length P of the coaxial piezoelectric cable within the cage is calculated according to:

$$P = (L+B) + \left(\sqrt{2} * B * (L-B+1)\right) + \left(2 * \sqrt{2} * \left(\sum_{K=1}^{B-1} B - k\right)\right), \text{ for } L \geq B$$

where:

$$L = \frac{a}{U}, B = \frac{b}{U}, \text{where } \{L, B \in \mathbb{Z} \mid L, B > 0\}.$$

Embodiments of the present invention include a cable assembly comprising a top sheet of a first material, having a major plane; a bottom sheet of a second material having substantially a same dimensional area as the top sheet; and at least one coaxial piezoelectric cable arranged in a coil between the top sheet and the bottom sheet and in a plane substantially parallel with the major plane of the top sheet.

Further embodiments include the cable assembly, comprising an encapsulating material substantially surrounding the top sheet, the bottom sheet, and the coaxial piezoelectric cable. Further embodiments include the cable assembly, wherein the first material comprises one of: acrylic, polycarbonate, plastic, one or more composites, silicone, or rubber. Further embodiments include the cable assembly, wherein the first material and the second material are the same. Further embodiments include the cable assembly, wherein the coil of the coaxial piezoelectric cable is arranged uniformly in a volume between the top sheet and the bottom sheet. Further embodiments include the cable assembly, wherein coil comprises a plurality of segments. Further embodiments include the cable assembly, wherein a distance from any portion of one segment to a closest different segment is based on a predetermined size, U. Further embodiments include the cable assembly, wherein the assembly is sized to substantially extend to fill an inside perimeter of a cage for a rodent. Further embodiments include the cable assembly, wherein the distance, U, is less than or equal to an average size of the rodent. Further embodiments include the cable assembly, wherein the top sheet comprises a rectangle comprising a width a and a length b, and the length P of a portion of the coaxial piezoelectric cable located between the top sheet and the bottom sheet is calculated according to:

$$P = (L+B) + \left(\sqrt{2} * B * (L-B+1)\right) + \left(2 * \sqrt{2} * \left(\sum_{k=1}^{B-1} B - k\right)\right), \text{ for } L \geq B$$

where:

$$L = \frac{a}{U}, B = \frac{b}{U}, \text{where } \{L, B \in \mathbb{Z} \mid L, B > 0\}.$$

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. Aspects of the invention were chosen and described in order to best explain the principles of the invention and the practical application, and to enable others of ordinary skill in the art to understand the invention for various embodiments with various modifications as are suited to the particular use contemplated.

As will be appreciated by one skilled in the art, the present invention may be embodied as a method, system, or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device 1418. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present invention may be written in an object-oriented programming language such as JAVA, SMALLTALK, C++ or the like. However, the computer program code for carrying out operations of the present invention may also be written in conventional procedural programming languages, such as the "C" programming language or similar programming languages. Additionally, functional programming languages, such as LABVIEW, ERLAND, OCAML, HASKELL, and the like, may be used for the computer program code to carry out operations of the present invention. The program code may execute entirely on the user's data analyzer 1400, partly on the user's data analyzer 1400, as a stand-alone software package, partly on the user's data analyzer 1400 and partly on a remote computer or entirely on the remote computer or server. In the latter scenario, the remote computer may be connected to the user's data analyzer 1400 through a local area network (LAN) or a wide area network (WAN), or the connection may be made to an external computer (for example, through the Internet using an Internet Service Provider). In some embodiments, the data analyzer 1400 may executed the code on a microcontroller.

The present invention is described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, data analyzer 1400, special purpose computer, or other programmable data processing apparatus to produce a machine, such that the instructions, which execute via the processor of the data analyzer 1400 or other programmable data processing apparatus, create means for implementing the functions/acts specified in the flowchart and/or block diagram block or blocks.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method for sensing an environment, comprising: confining a monitored live subject in an enclosure; detecting an effect on a coaxial piezoelectric cable resulting from the monitored live subject, wherein the coaxial piezoelectric cable is located at least proximate to the enclosure; and deriving information about a state of the monitored live subject based on the detected effect, wherein the enclosure comprises a cage.

2. The method of claim 1, wherein the monitored live subject comprises a mammal.

3. The method of claim 2, wherein the mammal comprises a rodent.

4. The method of claim 1, wherein the coaxial piezoelectric cable is in physical contact with at least a portion of the cage.

5. The method of claim 1, wherein the coaxial piezoelectric cable is one of a plurality of coaxial piezoelectric cables located at least proximate to the enclosure, the method further comprising: detecting a respective effect on each of a plurality of coaxial piezoelectric cables resulting from the monitored live subject; and deriving the information about the state of the monitored live subject based on the respective detected effects.

6. The method of claim 1, wherein: the cage comprises a plurality of walls and a floor, the floor aligned in a first plane substantially perpendicular to the plurality of walls; and the coaxial piezoelectric cable is located under the floor, aligned in a second plane substantially parallel to the first plane.

7. The method of claim 6, wherein a layout of the coaxial piezoelectric cable is arranged to provide uniform sensing coverage of the floor.

8. The method of claim 6, wherein the layout of the coaxial piezoelectric cable is arranged in a coil comprising a plurality of segments.

9. The method of claim 1, wherein the coaxial piezoelectric cable is encapsulated in a protective assembly, the protective assembly detachably positioned in physical contact with the cage.

10. The method of claim 9, wherein the protective assembly comprises: a top layer having a first surface area substantially the same as a floor of the cage; and a bottom layer having a second surface area substantially the same as the floor of the cage, wherein the coaxial piezoelectric cable is positioned between the top layer and the bottom layer.

11. The method of claim 1, comprising: supporting the enclosure on a rack structure.

12. The method of claim 11, wherein the coaxial piezoelectric cable is positioned between a surface of the rack structure and an outside surface of the enclosure.

13. The method of claim 12, wherein the surface of the rack structure provides mechanical amplification of the effect on the piezoelectric cable resulting from the monitored live subject.

14. The method of claim 1, wherein the information about the state of the monitored live subject relates to one or more of: activity levels, phases of sleep, respiratory effort, or heart rate.

15. A method for sensing an environment, comprising: confining a monitored live subject in an enclosure; detecting an effect on a coaxial piezoelectric cable resulting from the monitored live subject, wherein the coaxial piezoelectric cable is located at least proximate to the enclosure; and deriving information about a state of the monitored live subject based on the detected effect, wherein: the monitored live subject comprises a plurality of monitored live subjects; and the detected effect on the piezoelectric cable results from the plurality of monitored live subjects.

16. The method of claim 15, wherein the step of deriving comprises: deriving information about a respective state of each of the plurality of monitored live subjects based on the detected effect.

17. A system for sensing an environment, comprising: an enclosure configured to confine a monitored live subject; a coaxial piezoelectric cable positioned at least proximate to the enclosure; a receiver circuit, in electrical communication with the coaxial piezoelectric cable, to receive a signal indicative of an effect on the coaxial piezoelectric cable resulting from the monitored live subject when the monitored live subject is within the enclosure; a computer-readable memory, in electrical communication with the receiver circuit, to store data related to the signal received by the receiver circuit; and a signal conditioning circuit, in electrical communication with the coaxial piezo electric cable and the receiver circuit, to filter and amplify a raw signal received from the coaxial piezoelectric cable to produce the signal received by the receiver circuit.

18. The system of claim 17, wherein the receiver circuit comprises an analog-to-digital converter to convert the signal received by the receiver circuit to the data stored in the computer-readable memory.

19. The system of claim 17, comprising: a computer, in communication with the computer-readable memory, the computer comprising: a memory device storing executable instructions; and a processor coupled with the memory device, wherein the executable instructions, when executed by the processor, cause the processor to: derive information about a state of the monitored live subject based on the data stored in the computer-readable memory.

* * * * *